US012740694B2

(12) United States Patent
Diehl et al.

(10) Patent No.: US 12,740,694 B2
(45) **Date of Patent: *Sep. 22, 2026**

(54) LIGHTED SURGICAL ACCESS SYSTEM

(71) Applicant: Applied Medical Resources Corporation, Rancho Santa Margarita, CA (US)

(72) Inventors: Alex Diehl, Ladera Ranch, CA (US); Luis Salazar, Compton, CA (US); Andrew Nguyen, Rancho Santa Margarita, CA (US); Jonathan Rothschild, Huntington Beach, CA (US); Joel Velasco, Rancho Santa Margarita, CA (US); Khodr Saleh, Whittier, CA (US); Alexis Penaloza, Riverside, CA (US); Ralph Sias, Oceanside, CA (US); Tina Talwar, Rancho Santa Margarita, CA (US); Cory Hague, Aliso Viejo, CA (US); Boun Pravong, Rancho Santa Margarita, CA (US); Kennii Pravongviengkham, Rancho Santa Margarita, CA (US); Suraj Sharma, Rancho Santa Margarita, CA (US)

(73) Assignee: Applied Medical Resources Corporation, Rancho Santa Margarita, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 19/422,930

(22) Filed: Dec. 17, 2025

(65) Prior Publication Data

US 2026/0102061 A1 Apr. 16, 2026

Related U.S. Application Data

(63) Continuation of application No. 18/186,729, filed on Mar. 20, 2023, now Pat. No. 12,527,467, which is a (Continued)

(51) Int. Cl.
*A61B 1/07* (2006.01)
*A61B 1/313* (2006.01)
(Continued)

(52) U.S. Cl.
CPC .............. *A61B 1/07* (2013.01); *A61B 1/3132* (2013.01); *A61B 17/0293* (2013.01);
(Continued)

(58) Field of Classification Search
CPC ............ A61B 17/0293; A61B 17/3423; A61B 2090/306; A61B 90/30
See application file for complete search history.

(56) References Cited

U.S. PATENT DOCUMENTS 3,807,393 A 4/1974 McDonald
5,159,921 A 11/1992 Hoover
(Continued)

FOREIGN PATENT DOCUMENTS

DE 10 2016 114 129 A1 2/2018
WO WO 2004/075930 A2 9/2004
(Continued)

OTHER PUBLICATIONS

European Patent Office, The International Search Report and Written Opinion for International Application No. PCT/US2021/054124, entitled "Lighted Surgical Access System," mailed Jan. 17, 2022, 14 pgs.

(Continued)

*Primary Examiner* — Alexander K Garlen
(74) *Attorney, Agent, or Firm* — Patrick Ikehara

(57) ABSTRACT

The lighted surgical access system is provided that includes a circumferential retractor and a plastic optical fiber (POF) attached thereto. The circumferential retractor retracts and protects a patient's body opening while the POF illuminates the internal surgical site, body cavity and/or body opening.

14 Claims, 20 Drawing Sheets

Related U.S. Application Data continuation of application No. PCT/US2021/054124, filed on Oct. 8, 2021.

(60) Provisional application No. 63/248,319, filed on Sep. 24, 2021, provisional application No. 63/089,486, filed on Oct. 8, 2020.

(51) Int. Cl.
*A61B 17/02* (2006.01)
*A61B 17/34* (2006.01)
*A61B 90/30* (2016.01)

(52) U.S. Cl.
CPC .......... *A61B 17/3423* (2013.01); *A61B 90/30* (2016.02); *A61B 2090/306* (2016.02)

(56) References Cited

U.S. PATENT DOCUMENTS 5,353,786 A * 10/1994 Wilk .................... G02B 6/0005 600/249
5,522,791 A 6/1996 Leyva
5,810,721 A 9/1998 Mueller et al.
5,865,729 A 2/1999 Meehan et al.
5,906,577 A 5/1999 Beane et al.
6,048,309 A 4/2000 Flom et al.
6,142,935 A 11/2000 Flom et al.
6,142,936 A 11/2000 Beane et al.
6,162,172 A 12/2000 Cosgrove et al.
6,352,531 B1 3/2002 O'Connor et al.
6,409,391 B1 6/2002 Chang
6,428,473 B1 8/2002 Leonard et al.
6,440,063 B1 8/2002 Beane et al.
6,464,406 B1 10/2002 Yarita et al.
6,497,654 B1 12/2002 Leonard et al.
6,504,985 B2 1/2003 Parker et al.
6,626,582 B2 9/2003 Farrar et al.
6,814,700 B1 11/2004 Mueller et al.
6,939,296 B2 9/2005 Ewers et al.
7,008,377 B2 3/2006 Beane et al.
7,066,931 B2 6/2006 O'Connor et al.
7,182,524 B2 2/2007 Kramer et al.
7,223,233 B2 5/2007 Branch et al.
7,510,524 B2 3/2009 Vayser et al.
7,645,275 B2 1/2010 O'Connor et al.
7,703,987 B2 4/2010 Kramer et al.
7,758,500 B2 7/2010 Boyd et al.
7,901,353 B2 3/2011 Vayser et al.
7,909,761 B2 3/2011 Banchieri et al.
7,955,257 B2 6/2011 Frasier et al.
7,959,651 B2 6/2011 Branch et al.
8,088,066 B2 1/2012 Grey et al.
8,105,236 B2 1/2012 Malandain et al.
8,162,824 B2 4/2012 Vayser et al.
8,282,677 B2 10/2012 O'Connor et al.
8,303,497 B2 11/2012 Aferzon
8,317,693 B2 11/2012 Grey et al.
8,409,089 B2 4/2013 Michaeli et al.
8,430,813 B2 4/2013 Selover et al.
8,454,504 B2 6/2013 Michaeli et al.
8,480,566 B2 7/2013 Farr
8,550,993 B2 10/2013 Aferzon
8,636,658 B2 1/2014 Su et al.
8,641,608 B2 2/2014 Voegele et al.
8,663,102 B2 3/2014 Michaeli et al.
8,684,577 B2 4/2014 Vayser
8,708,896 B2 4/2014 Vayser et al.
8,864,662 B2 10/2014 Grey et al.
9,005,115 B2 4/2015 Vayser
9,060,707 B2 6/2015 Grey et al.
9,072,455 B2 7/2015 Vayser et al.
9,072,501 B2 7/2015 Menchaca et al.
9,161,820 B2 10/2015 Mark et al.
9,186,175 B2 11/2015 Mark et al.
9,216,015 B2 12/2015 Wilson
9,254,126 B2 2/2016 Frasier et al.
9,265,523 B2 2/2016 Mark et al.
9,271,637 B2 3/2016 Farr
9,282,878 B2 3/2016 Grey et al.
9,357,987 B2 6/2016 Aferzon
9,381,012 B2 7/2016 Su
9,386,974 B2 7/2016 Wilson
9,387,010 B2 7/2016 Mark et al.
9,468,366 B2 10/2016 Grey et al.
9,480,855 B2 11/2016 DiMauro et al.
9,504,373 B2 11/2016 Vayser et al.
9,579,121 B2 2/2017 Mark et al.
9,615,884 B2 4/2017 Armour et al.
9,622,777 B2 4/2017 Mark et al.
9,757,147 B2 9/2017 Mark et al.
9,770,261 B2 9/2017 Mark et al.
9,907,545 B2 3/2018 Galloway et al.
9,949,730 B2 4/2018 Hart et al.
9,968,414 B2 5/2018 Wilson
9,968,415 B2 5/2018 Wilson
9,986,901 B2 6/2018 Grey et al.
10,085,649 B1 10/2018 Valko et al.
10,088,638 B2 10/2018 Yajima
10,098,626 B2 10/2018 Gharibi Loron
10,105,042 B2 10/2018 Davis et al.
10,143,366 B2 12/2018 Mark et al.
10,172,514 B2 1/2019 Davis et al.
10,172,525 B2 1/2019 Davis et al.
10,307,183 B2 6/2019 Mark et al.
10,349,927 B2 7/2019 Galloway et al.
10,349,930 B2 7/2019 DiMauro et al.
10,376,281 B2 8/2019 Davis et al.
10,398,318 B2 9/2019 Davis et al.
10,405,941 B2 9/2019 Grey et al.
10,413,169 B2 9/2019 Davis et al.
10,449,340 B2 10/2019 Mark et al.
2004/0127772 A1* 7/2004 Ewers .................... A61B 90/30 600/212
2005/0171408 A1 8/2005 Parker
2005/0209510 A1 9/2005 Bonadio et al.
2006/0161049 A1 7/2006 Beane et al.
2006/0247500 A1 11/2006 Voegele et al.
2007/0100210 A1 5/2007 Selover et al.
2007/0100211 A1 5/2007 Selover et al.
2008/0194973 A1 8/2008 Imam
2008/0319432 A1 12/2008 Ely et al.
2009/0118587 A1 5/2009 Voegele et al.
2011/0118553 A1 5/2011 Stopek
2011/0257488 A1 10/2011 Koyama et al.
2012/0041268 A1 2/2012 Grey et al.
2012/0101341 A1 4/2012 Malandain et al.
2012/0289816 A1 11/2012 Mark et al.
2013/0012770 A1 1/2013 Su
2013/0018230 A1* 1/2013 Su ............................ A61B 1/32 600/208
2013/0032628 A1 2/2013 Li et al.
2013/0217975 A1 8/2013 Selover et al.
2014/0039265 A1 2/2014 Aferzon
2014/0153278 A1 6/2014 Vayser
2014/0343366 A1 11/2014 Coe et al.
2015/0157307 A1 6/2015 Su
2015/0173596 A1 6/2015 Vayser
2016/0128722 A1 5/2016 Mark et al.
2016/0220240 A1 8/2016 Hart et al.
2016/0270816 A1 9/2016 Mather et al.
2016/0324402 A1 11/2016 Yajima
2017/0035275 A1 2/2017 Yajima et al.
2017/0042525 A1 2/2017 DiMauro et al.
2017/0095310 A1 4/2017 Vayser et al.
2017/0095311 A1 4/2017 Vayser et al.
2017/0100022 A1 4/2017 Vayser et al.
2017/0100023 A1 4/2017 Vayser
2017/0224206 A1 8/2017 Vayser
2017/0265734 A1 9/2017 Vayser
2017/0367731 A1 12/2017 Mark et al.
2018/0021032 A1 1/2018 DiMauro et al.
2018/0064322 A1 3/2018 Klubben, III et al.
2018/0206882 A1 7/2018 Davis et al.
2018/0249902 A1 9/2018 Grey et al.

(56) References Cited

U.S. PATENT DOCUMENTS

| | | | |
|---|---|---|---|
| 2019/0000435 | A1 | 1/2019 | Galloway et al. |
| 2019/0053826 | A1 | 2/2019 | Bush, Jr. et al. |
| 2019/0099070 | A1 | 4/2019 | Mark et al. |
| 2019/0117254 | A1 | 4/2019 | Mark et al. |
| 2019/0133433 | A1 | 5/2019 | Davis et al. |
| 2019/0167246 | A1 | 6/2019 | DiMauro et al. |
| 2019/0200853 | A1 | 7/2019 | Alvarez Gallego et al. |
| 2019/0239923 | A1 | 8/2019 | Mark et al. |

FOREIGN PATENT DOCUMENTS

| | | | |
|---|---|---|---|
| WO | WO 2012/159117 | A1 | 11/2012 |
| WO | WO 2017/151754 | A1 | 9/2017 |
| WO | WO 2019/215354 | A1 | 11/2019 |

OTHER PUBLICATIONS

The International Bureau of WIPO, International Preliminary Report on Patentability for International Application No. PCT/US2021/54124, entitled "Lighted Surgical Access System," dated Apr. 20, 2023, 7 pgs.

European Patent Office, The International Search Report and Written Opinion for International Application No. PCT/US2021/54312, entitled "Lighted Surgical Access System," mailed Jan. 14, 2022, 13 pgs.

The International Bureau of WIPO, International Preliminary Report on Patentability for International Application No. PCT/US2021/54312, entitled "Lighted Surgical Access System," dated Apr. 20, 2023, 6 pgs.

* cited by examiner

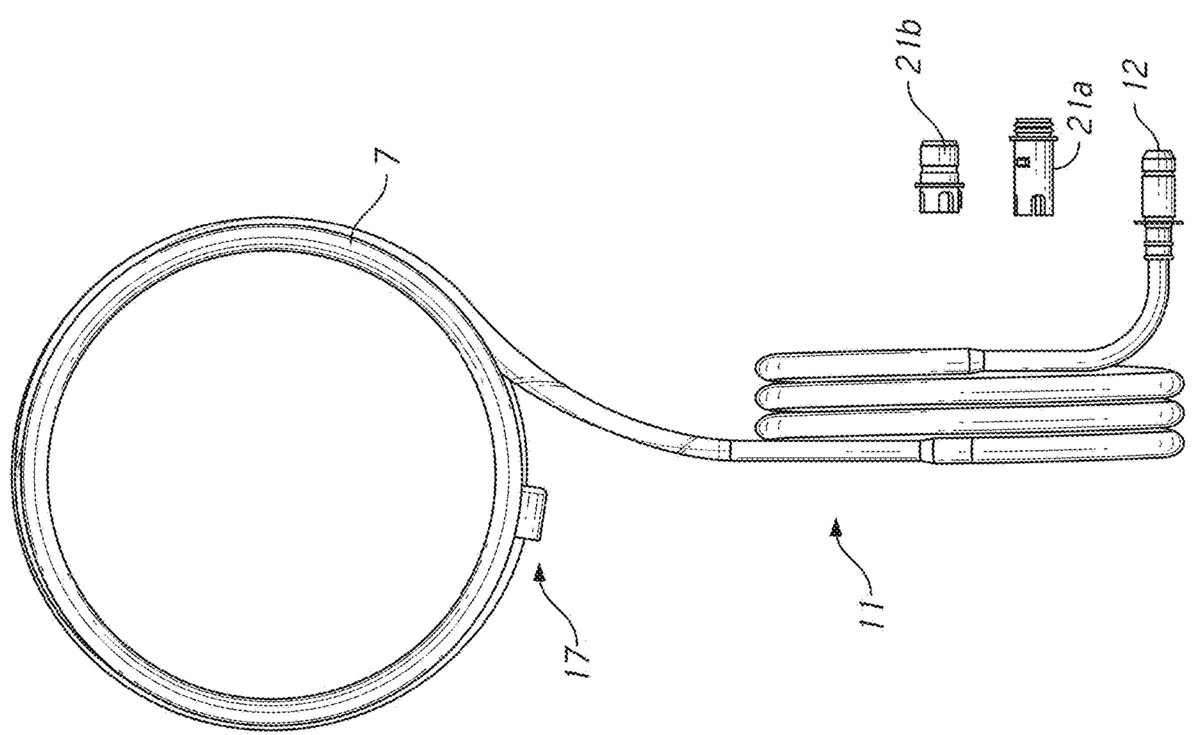
7
21b
21a
12
17
11

5
9
11
7
16
8
3

12
21b
21a
14

9
8
7
16

LIGHTED SURGICAL ACCESS SYSTEM

CROSS-REFERENCE TO RELATED APPLICATIONS

This is a continuation of U.S. patent application Ser. No. 18/186,729, filed Mar. 20, 2023 which is a continuation of International Patent Application No. PCT/US2021/054124, filed on Oct. 8, 2021, that claims priority to and benefit of U.S. Provisional Patent Application Serial Nos. 63/089,486, filed on Oct. 8, 2020, and 63/248,319, filed on Sep. 24, 2021, all of which are incorporated herein by reference in their entirety.

BACKGROUND

The present application is generally directed to systems and methods for illuminating a surgical site and more particularly, lighted circumferential protectors-retractors and systems and methods thereof for illuminating internal surgical sites.

Proper illumination of a surgical site facilitates a surgical procedure, assisting the surgeon or medical personnel in the placement and operation of surgical instruments within the limited space confines of a patient's body cavity. Overhead surgical lamps are ubiquitous in operating rooms but are limited in providing effective illumination largely because of their positioning far outside the surgical site (e.g., incision or patient opening). Also, as the light comes from a limited direction, e.g., only one or two directions, it is difficult to avoid casting shadows that limit the visibility of the surgical site. In addition, the area of illumination is not tightly focused, causing glare around the site and diminishing the visual contrast. The amount of light that can illuminate the internal anatomy or internal surgical site is also restricted by the size of the incision or opening, becoming extremely challenging to achieve sufficient lighting as the size of the incision or opening is diminished. The convenience of overhead lamps is further reduced by the need for frequent readjustment to find a proper angle, especially when a surgical procedure requires repositioning of the patient.

Surgical headlamps suffer from many of the same drawbacks, including the problem of casting shadows from a unidirectional light, glare around the incision, and limited light entering the incision or opening. Such lamps can also be inconvenient as they are often bulky or require continuous concentration to keep the light properly directed. Lighted single point retractors aim to solve some of the problems with the ineffectiveness of overhead lights and headlamps, though they sacrifice some convenience because they must be held by hand. These lighted retractors also fail to provide circumferential illumination to the surgical site. Furthermore, such devices often provide unidirectional light without being able to illuminate deeply inside the patient's cavity. Additionally, often the direction of the light beams cannot be adjusted without losing traction. Other lighting systems fail to account for or overcome the challenges of obstruction from surrounding tissue or the device itself along with thermal, luminescence output or other similar performance, manufacturing, and procedural issues.

SUMMARY

In accordance with various embodiments, a lighted surgical access system is provided. The lighted surgical access system comprises a circumferential protector and a plastic optical fiber (POF) connectable to the circumferential protector. In various embodiments, the circumferential protector comprises an outer ring, an inner ring, a sheath, or any combination thereof. In various embodiments, the POF is connectable to a light generator or source. In various embodiments, the POF comprises a plurality of scoring or cuts. In various embodiments, the POF illuminates the internal surgical site, body cavity, body opening or any combination thereof.

In accordance with various embodiments, a lighted surgical access system comprises an outer ring, an inner ring and a sheath having a proximal end connected to the outer ring arranged to be placed outside of a body cavity or externally to an internal surgical site and a distal end connected to the inner ring arranged to be placed inside of a body cavity or proximal to an internal surgical site. The sheath delimits an access channel extending from the outer ring to the inner ring. The lighted surgical access system comprises a light generator and a POF. The light generator is connectable to the POF, a laparoscope or both.

In various embodiments, the POF comprises a POF leader being a proximal portion of the POF and a POF tail being a distal portion of the POF and in various embodiments, the POF leader extends beyond the outer ring and is connectable to the light generator. The lighted surgical access system further comprises a sleeve connected to a distal portion of the sheath and spaced from the inner ring. The sleeve extends radially around the distal portion of the sheath and at least the POF tail is positioned and/or encased within the sleeve.

In accordance with various embodiments, a lighted surgical access system to illuminate internally a body cavity is provided. In various embodiments, the lighted surgical access system comprises an outer ring arranged to be placed outside of a body cavity, an inner ring arranged to be placed inside of the body cavity, and a sheath having a proximal end connected to the outer ring and a distal end connected the inner ring with the sheath delimiting a lumen with an access channel extending from the outer ring to the inner ring. In various embodiments, the light surgical access system comprises a light generator arranged to be connectable to a light emitter or the like.

In various embodiments, the light surgical access system comprises a light generator arranged to be connectable to a laparoscope. In various embodiments, the light surgical access system comprises a plastic optical fiber (POF) comprising a POF leader being a proximal portion of the POF and a POF tail being a distal portion of the POF with the POF leader extending beyond the outer ring and connectable to a light generator. In various embodiments, the light surgical access system comprises a sleeve connected to a distal portion of a sheath and spaced from an inner ring. In various embodiments, the light surgical access system comprises a sleeve extending radially around the distal portion of the sheath and a POF tail being positioned within the sleeve. In various embodiments, a POF tail comprises a plurality of cuts. In various embodiments, a POF tail comprises a plurality of cuts that are disposed on a side of the POF tail that faces away from the inner ring and/or are angled.

In various embodiments, a POF tail comprises a non-transparent material covering a portion of the POF tail that has a plurality of cuts. In various embodiments, a POF tail comprises a reflective material disposed between a non-transparent material and a plurality of cuts. In various embodiments, a non-transparent material covers a POF leader and/or a POF tail. In various embodiments, a POF leader comprises a reflective material disposed between a non-transparent material and the POF leader. In various embodiments, a POF leader comprises a plurality of cuts.

In various embodiments, a light cable is connectable to a light generator and a proximal end of a POF leader. In various embodiments, a light cable is connectable to a light generator and an adaptor or a connector. In various embodiments, an adaptor or connector is connectable to a proximal end of a POF leader and/or comprises an adjustable opening arranged to connect to a light cable. In various embodiments, an adaptor or connector comprises a clamp arranged to adjust an adjustable opening. In various embodiments, a first light cable, a second light cable, and/or a double-sided adaptor are provided. In various embodiments, a double-sided adaptor has a first side connectable to a first light cable and a second side connectable to a connector on a proximal end of a POF leader, the first side of the adaptor also being connectable to the connector and the second side being connectable to a second light cable. In various embodiments, the first side of the double-sided adaptor has a connection interface different from a connection interface of the second side of the double-sided adaptor.

In various embodiments, a reflective material positioned within a sleeve connectable or connected to a sheath. In various embodiments, a sheath has an inner surface, an outer surface, and a sleeve is connected to the outer surface of the sheath. In various embodiments, a reflective material is positioned on an inner surface of a sheath. In various embodiments, a distal end of a POF tail has an angled end profile. In various embodiments, an end cap is connected to a distal end of a POF tail. In various embodiments, a reflective material is attached to an end cap. In various embodiments, a light generator is arranged to be connectable, optionally, to a laparoscope. In various embodiments, the light surgical access system comprises a light generator arranged to be connectable to an optional laparoscope. In various embodiments, a POF leader is connectable to a light generator and a POF tail. In various embodiments, a POF tail comprises a plurality of cuts disposed on one side of the POF tail. In various embodiments, a sleeve extends around the distal portion of the sheath and has a channel through which a POF tail extends therethrough. In various embodiments, a sleeve is sealed to a distal portion of a sheath and is impermeable. In various embodiments, a light generator comprises a Xeon light source, a light output of at least 1500 lumens, and/or a 300-watt light source.

Many of the attendant features of the present inventions will be more readily appreciated as the same becomes better understood by reference to the foregoing and following description and considered in connection with the accompanying drawings.

BRIEF DESCRIPTION OF THE DRAWINGS

The present inventions may be better understood taken in connection with the accompanying drawings in which the reference numerals designate like parts throughout the figures thereof.

FIG. 2 is a bottom view of a lighted surgical access system in accordance with various embodiments of the present invention.

DETAILED DESCRIPTION

Figure 1:
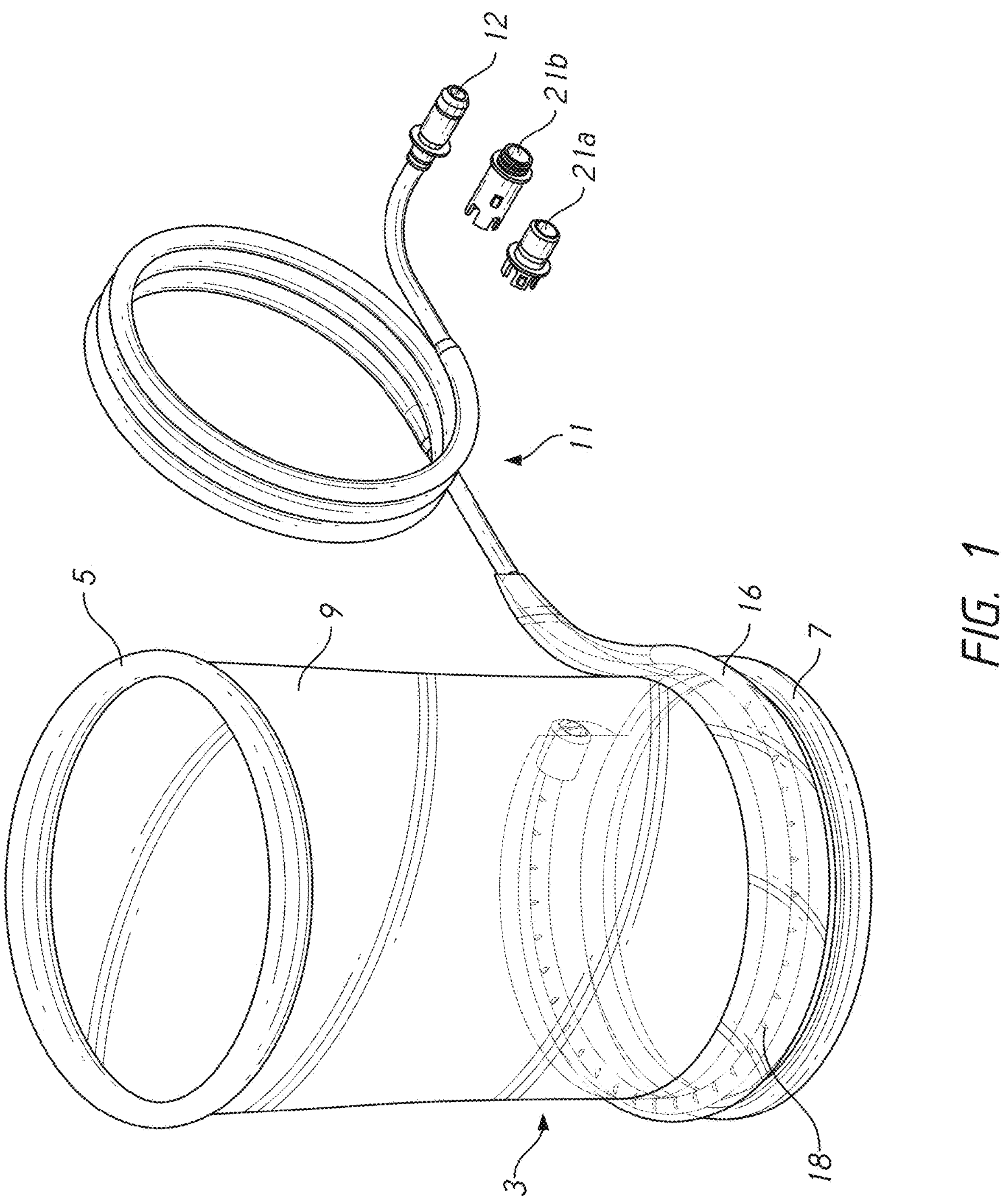
FIG. 1 is a perspective view of a lighted surgical access system in accordance with various embodiments of the present invention.
Figure 3:
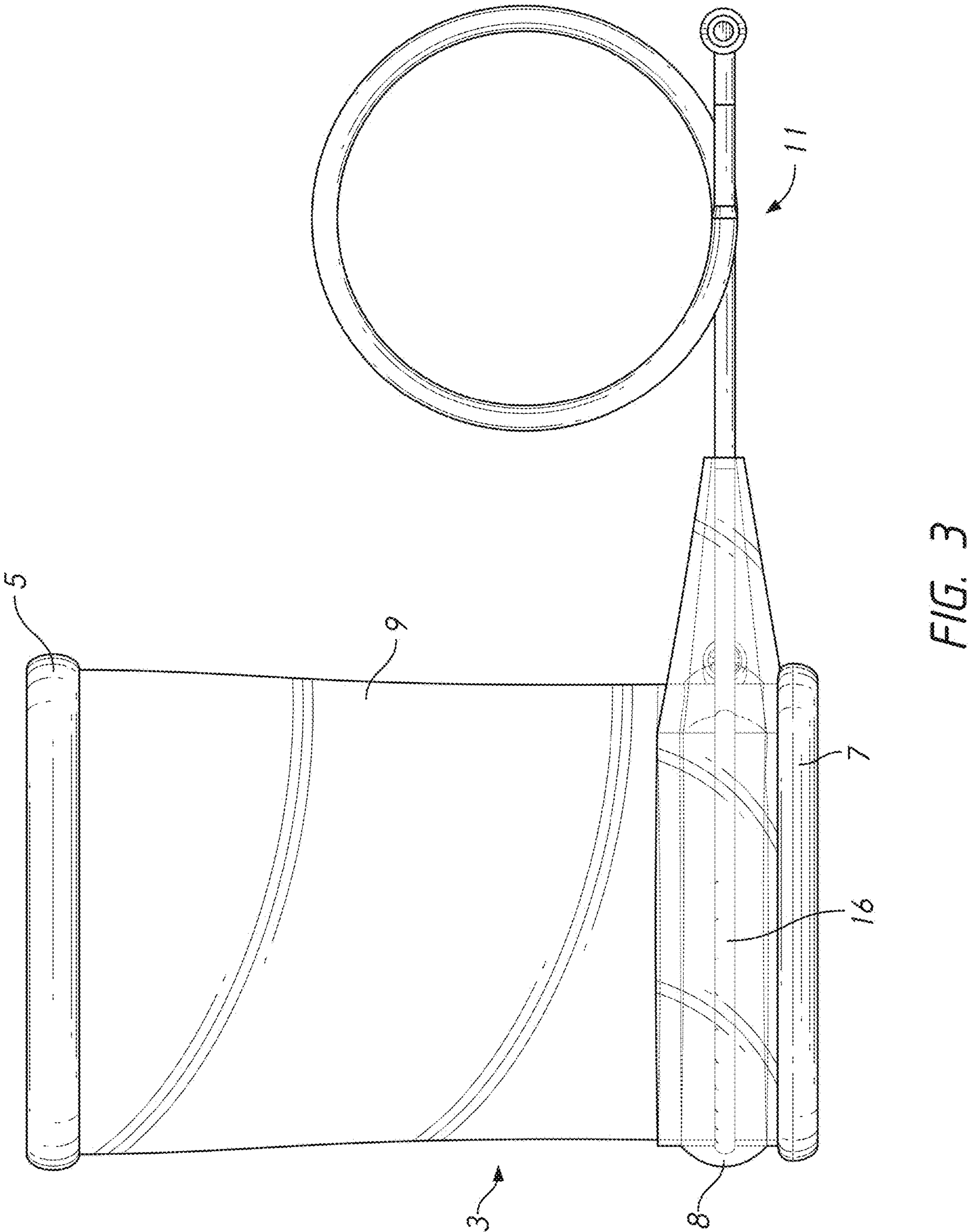
FIGS. 3-4 are side views of a lighted surgical access system in accordance with various embodiments of the present invention.
Figure 4:
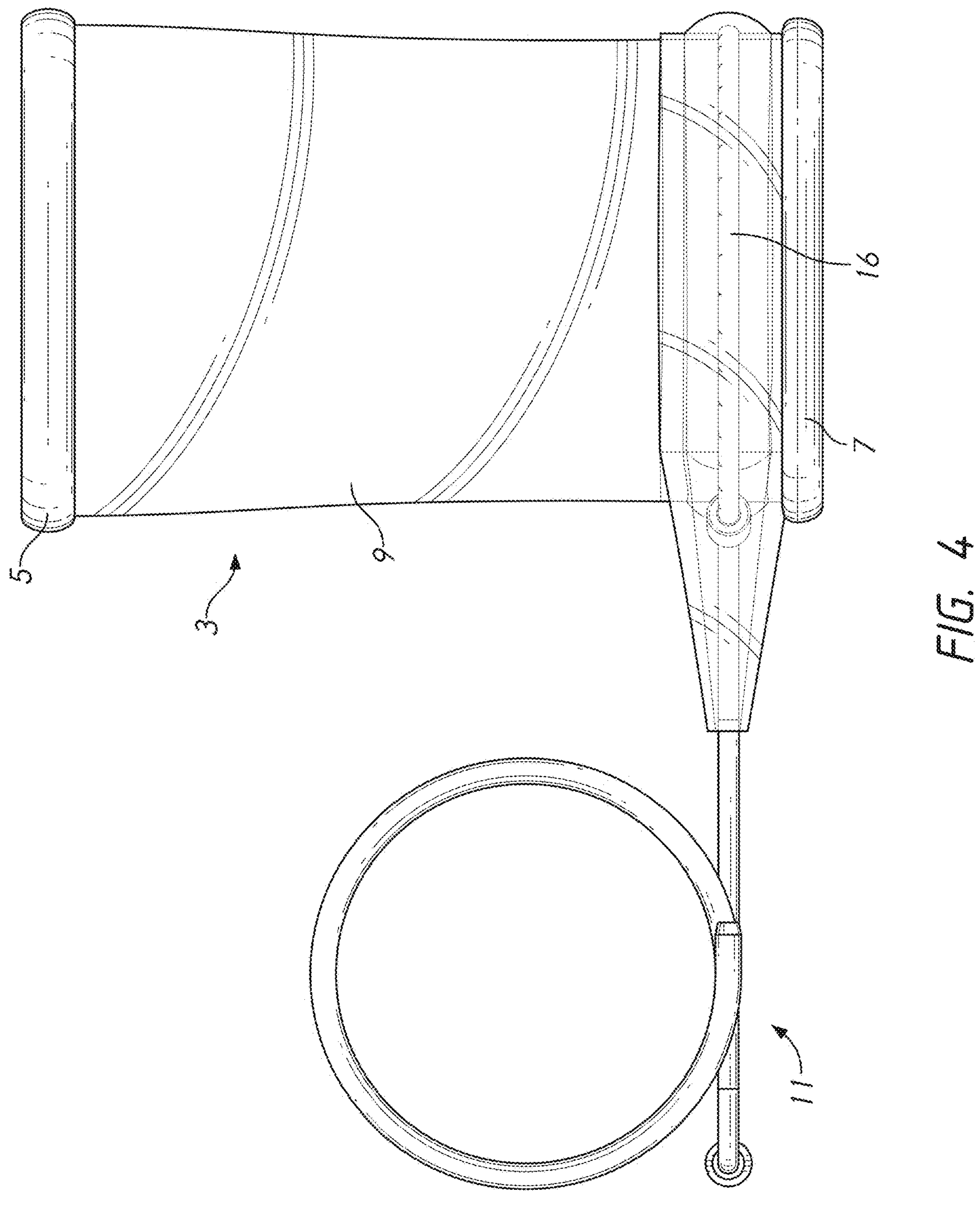

In accordance with various embodiments, lighted surgical access systems are provided, and various views of various embodiments of exemplary lighted surgical access systems and aspects thereof are shown in FIGS. 1-21D. The lighted surgical access system, in various embodiments, includes a protector/retractor 3 (hereinafter referred to as "retractor") providing circumferential or 360 degrees of protection and/or retraction of an opening or orifice of a patient. The lighted surgical access system creates and thus provides unobstructed and illuminated access into a patient's body or cavity. The retractor comprises an outer ring or support 5 and an inner ring or support 7. The inner and outer rings are connected by a film, fabric, membrane, or sheath 9. The retractor is adjustable in length by rolling the sheath around the outer ring and such adjustment can apply a retraction or radial force to retract or enlarge an opening in a patient. The retractor in various embodiments is adjustable in length or otherwise adjustable to accommodate different patient body types or body wall thickness. In various embodiments, the retractor has a fixed or predetermined length and/or is not adjustable in length by rolling the outer ring or other similar arrangements. The outer ring 5 is configured to be placed outside of the patient for ease of accessibility, adjustment of the retraction force and/or placement of the lighted surgical access system. In various embodiments, the sheath defines a working or access channel extending from its proximal end to its distal end and the lighted surgical access system provides unobstructed and illuminated access along and/or within the access channel defined by a sheath 9.

The retractor is sufficiently flexible to be atraumatic when the retractor is deployed or otherwise placed through and disposed in the opening of the patient. In various embodiments, the outer diameter or periphery of the retractor in operation and/or, as deployed, is delimited or is no larger than the outer diameter of the inner and/or outer rings. In various embodiment, the sheath 9 is made of an elastomeric or non-metallic material to be atraumatic and/or not or minimally thermally conductive when the retractor is in operation or deployed or otherwise placed through and disposed in the opening of the patient. In various embodiments, the sheath is made of one or more layers of material and in various embodiments is anisotropic, e.g., stretchable or extendable longitudinally but not or minimally radially, being made of or including one or more layers of a fabric or similar materials with such anisotropic characteristics.

Connected to a distal portion of the sheath 9 of the retractor is a light carrier, e.g., a plastic optical fiber (POF) 11. In various embodiments, the POF 11 is an elongate tube or tubular-like structure and/or having a core covered or encased in an outer cladding. The POF 11 has a distal portion attached to the distal portion of the sheath and for ease of readability is herein referred to as "POF tail" 16. The POF 11 also has a proximal portion configured to extend from the POF tail 16 or an intermediary portion therebetween. The proximal portion of the POF, for ease of readability, is herein referred to as "POF leader" 14. The POF tail or portions thereof is coupled to the sheath 9 of the retractor. In various embodiments, the POF tail or portions thereof is coupled to the sheath 9 by a sleeve 8.

As illustrated, in various embodiments, the POF 11 is attached to the sheath 9 of the retractor via a sleeve 8. The sleeve 8 in various embodiments surrounds all or at least a portion of an outer periphery of a distal portion of the sheath. The sleeve is configured to house a distal portion of the POF or the POF tail 16 and in various embodiments provides a channel in which the POF extends therethrough. The sleeve 8 in various embodiments is heat sealed on its proximal and distal portions relative to a longitudinal axis of the sheath enclosing and encompassing the POF. The sleeve 8 is configured to create a barrier to prevent blood or other foreign matter from entering the sleeve, obstructing the POF and/or absorbing the light emitted from the POF. In various embodiments, the sleeve 8 anchors the POF to the sheath 9 of the retractor and thus further assists in preventing the POF from being dislodged or otherwise removed from the sheath. The sleeve 8, in various embodiments, anchors the POF from independently moving lengthwise or longitudinally along the sheath or at least not beyond the confines of the sleeve. As such, in various embodiments, the sheath's placement determines the placement of the sleeve and thus the POF.

In various embodiments, the sleeve is embedded or otherwise integrated into the sheath 9 of the retractor. In various embodiments, the sheath includes at least two walls, e.g., an inner and outer wall, with the POF tail 16, sleeve 8 and/or portions thereof placed between the walls of the sheath. An opening to access and place the POF tail between the walls may be heat sealed or otherwise closed to prevent foreign matter from entering. In various embodiments, a seal 24 is place on one end of the sleeve 8 to prevent foreign matter from entering the seal and in various embodiments, the seal is placed between the POF tail 16 and the POF leader 14. Heat seals or the like below and/or above can be used to anchor the POF from independently moving lengthwise or longitudinally along the sheath or at least not beyond the confines of the sleeve. The heat seals may extend circumferentially around the sheath or only along one or more portions thereof. In various embodiments, the sleeve is made of one or more layers of material. In various embodiments, light output may be increased by covering the POF tail with a reflective material 22. The reflective material reflects escaping light back into the POF. In various embodiments, reflective material is place between the sleeve 8 and the sheath 9 or portions thereof. In various embodiments, reflective material is integrated with the sleeve 8 or portions thereof, e.g., an upper portion to further reflect down or distally and into an internal surgical site.

In various embodiments, a light generator or source is connectable to the POF. In various embodiments, the light generator or source is a light box 40, tower or the like configured to be connected to a laparoscope or endoscope. An endoscope may be connected to the light tower via a light cable 30 in which one end 31 is connected to the light tower and the other end 32 to the endoscope. As such, the light cable is configured to be connectable to a light tower or similar light source that is configured to supply light to a surgical laparoscope or endoscope. In various embodiments, the light source is provided by a surgical laparoscope or endoscope and/or its light source connected thereto. In various embodiments, the light source has a power supply or source and/or a controller to adjust the light output of the light source.

The light source being a source that supplies light to endoscope and laparoscope provides convenience to the user and eases operation of the lighted surgical access device, as such a source is often conveniently available in most surgical environments. Additionally, such sources also place electronic components and/or non-sterile components away from surgical site and can further provide the convenience of adjusting the light output of the light source and thus the POF connected thereto. It should however be appreciated that other sources of light may be provided or otherwise connected to the lighted surgical access device to supply light to the POF. As such, such described light sources should not be construed as limited but rather examples of a source of light for the POF. However, the light source either by itself or through other connections, adaptors, amplifiers, or the like provides sufficient lumens or light output to illuminate the internal surgical site and/or the access channel via the connected POF. In various embodiments, the light source is a Xeon light source, a 300-watt light source, generates a light output of at least 1500 lumens, or any combination thereof. In various embodiments, the light source comprises of one or more light emitting diodes ("LEDs"). In various embodiments, the light source, e.g., one or more LEDs or the like, is connectable to the light cable, a connector, an adaptor, the POF or any combination thereof. In various embodiments, the light source is battery powered.

In accordance with various embodiments, POFs are described throughout the description and it should be appreciated that POFs are notably different from LEDs or the like in that no metal, semiconductor or similar electronic or electronic related components are located within or provided therewith in POFs. As such, potential undesirable non-biocompatible components can be avoided with POFs relative to LEDs and the like. Other manufacturing or operational options are also available through the use of POFs versus LEDs and the like, such as the use of a single POF to vary the illumination at an internal surgical site versus multiple LEDs to provide similar illumination or coverage. Additionally, without electronic or other potentially sensitive material, the ease of sterilization or the potential range of sterilization techniques that can be used for the POF and/or the lighted surgical access system is enhanced.

In various embodiments, the lighted surgical access system includes one or more adapters or adaptors 21 and/or connectors 12 configured to provide a continuation between the POF and a light source, a light cable and/or an intermediary connection between the light source and/or the light cable. This continuation minimizes light loss and decreases the temperature experienced by the adaptor and/or connector as light is directly transferred from the light cable, source and/or intermediary to the POF without gaps or spaces, e.g., an air gap. In various embodiments, the continuation is provided by a flush or near flush contact or similar connections in which gaps or spaces between the POF and a light source, light cable and/or an intermediary connection between the light source and/or the light cable are minimized or eliminated. In various embodiments, the lighted surgical access system includes one or more adapters or adaptors 21 and/or connecters or connectors 12 configured to provide a flush or near flush contact between the POF and a light source, a light cable and/or an intermediary connection between the light source and/or the light cable.

In various embodiments, the adaptor and/or connector is made of plastic, metal or the like having high heat dissipation properties. In various embodiments, the adaptor and/or connector is made of or coated with a heat insulated material arranged to minimize heat transfer to other components, user and/or patient.

Figure 19:
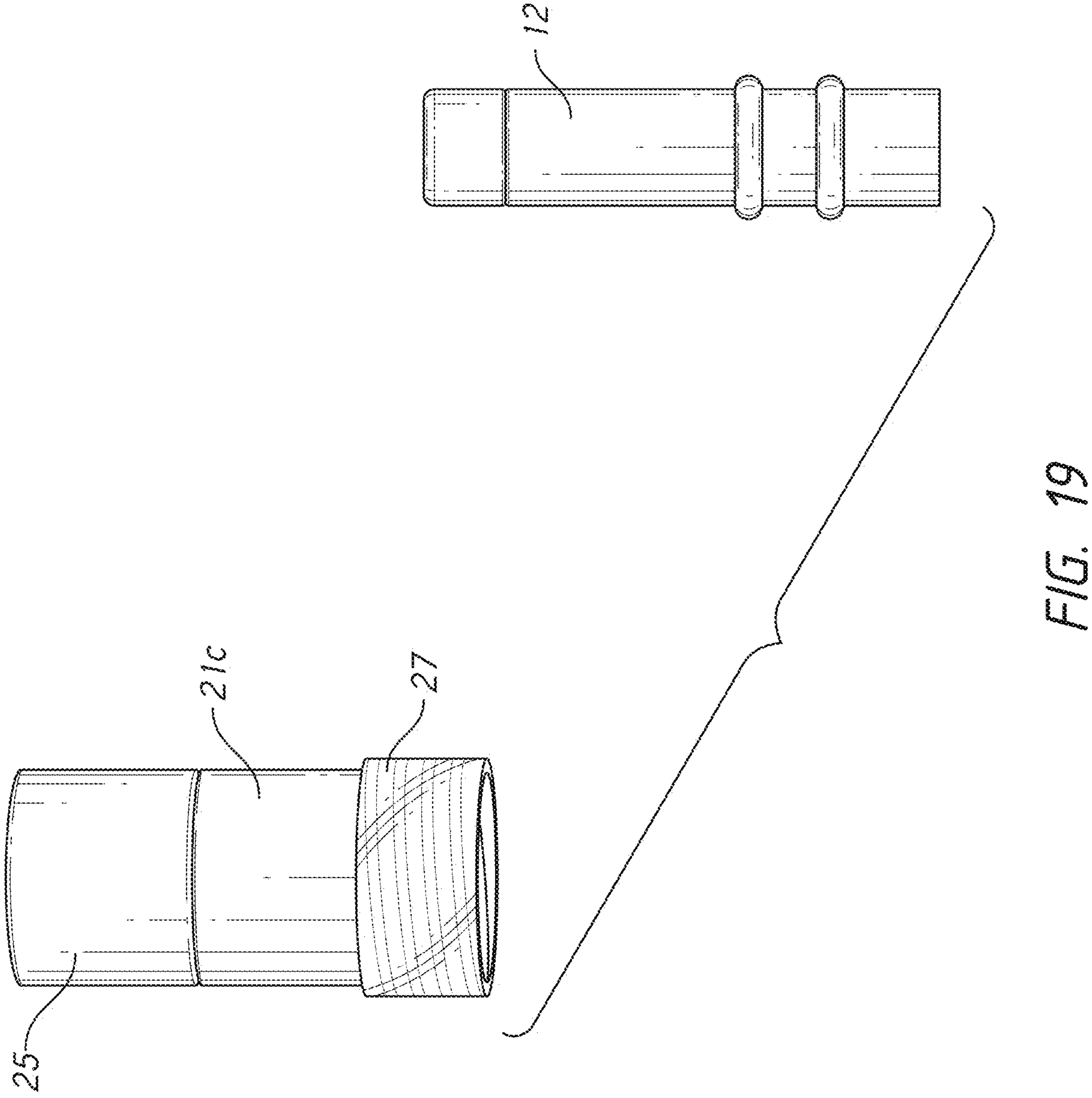
FIG. 19 are side views of an adaptor in accordance with various embodiments of the present invention.
Figure 20:
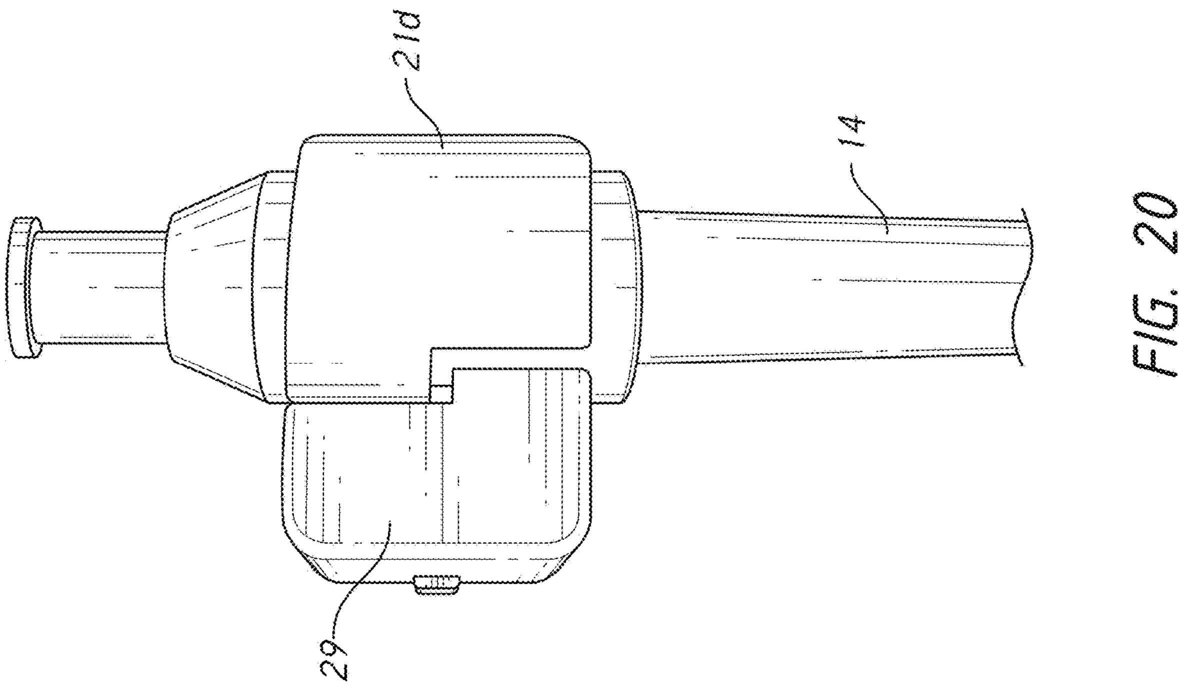
FIG. 20 is a side view of an adaptor in accordance with various embodiments of the present invention.
Figures 21A, 21B, 21C, 21D:
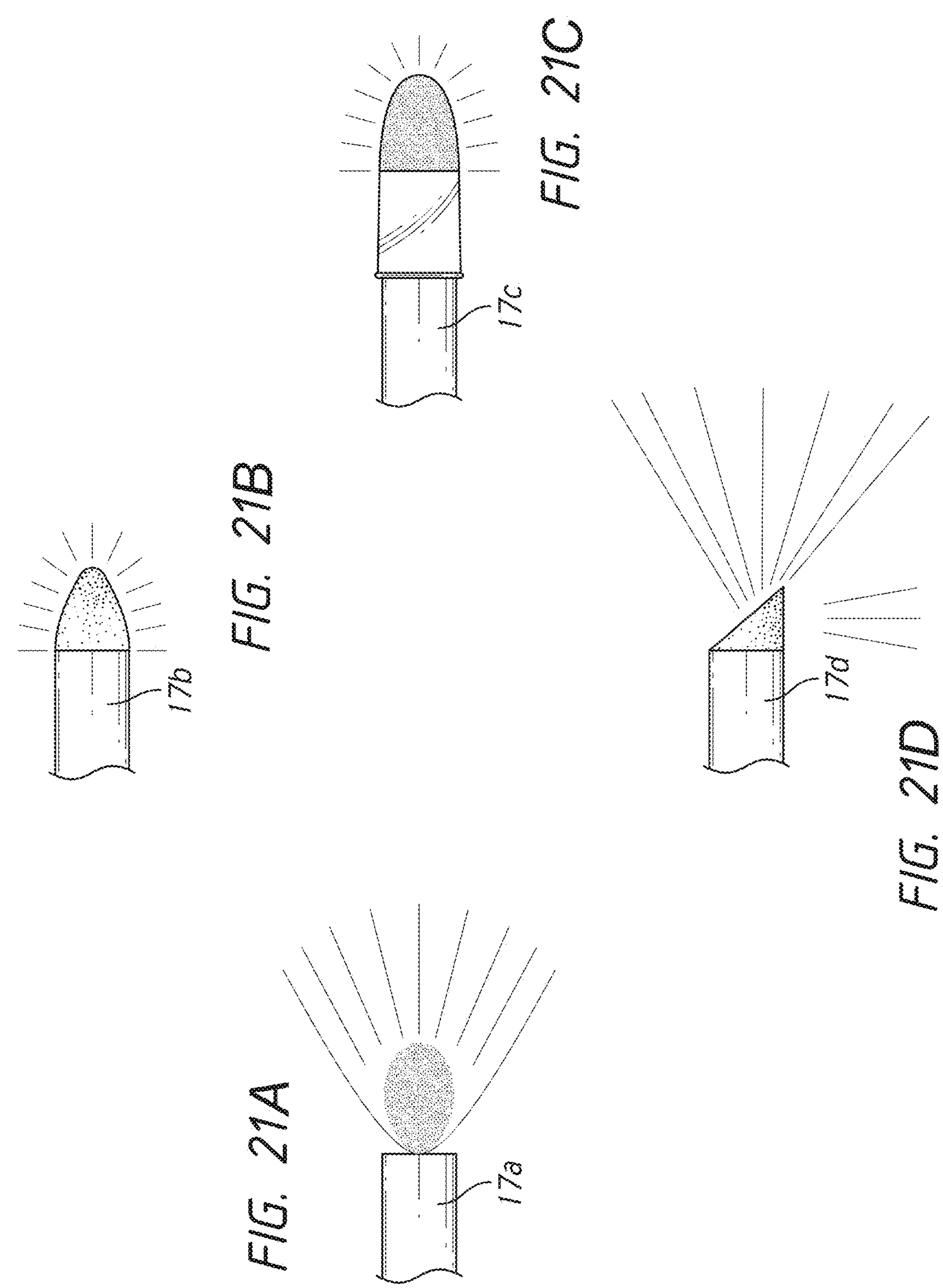
FIG. 21A is an end profile of a plastic optical fiber in accordance with various embodiments of the present invention.
FIG. 21B is an end profile of a plastic optical fiber in accordance with various embodiments of the present invention.
FIG. 21C is an end profile of a plastic optical fiber in accordance with various embodiments of the present invention.
FIG. 21D is an end profile of a plastic optical fiber in accordance with various embodiments of the present invention.

In various embodiments, the adaptor provides a user with the ability to interchange adaptor connection type based on their need and/or the available light cables, sources and/or intermediary connections. In various embodiments, the adaptor is interchangeable and/or double-sided. For example, as illustrated in FIG. 19, adaptor 21*c* is double-sided having one side 25 with an interface arranged to engage and secure with a first predetermined type or types of connections to light cables and/or light sources and an opposing or flip side 27 with an interface arranged to engage and secure with a second or different predetermined type or types of connections to light cables and/or light sources. Both sides 25, 27 of the adaptor 21*c* are arranged to engage and secure with the connector 12 of the POF 11. In various embodiments, sides 25, 27 connects and secures the adaptor to respective connections through threads, clips, snap-fits, keyways, bayonets or other various interfaces or interfacing features. An adaptor in various embodiments connects with a fixed ACMI adaptor using threads or snap on features. In various embodiments, the connector and/or adaptor, e.g., adaptor 21*d*, includes levers or arms, e.g., arm 29, configured to enlarge or retract an inner diameter or opening to open/close or clamp around a connection or end of the light source, light cable, and/or an intermediary connection, e.g., an adaptor or additional cables. In various embodiments, one end of the adaptor and/or connector has an adjustable opening or clamp interface, e.g., adaptor 21*d* as shown in FIG. 20, and in other various embodiments, the adaptor and/or connector has both ends with adjustable openings or clamp interfaces. In various embodiments, the adaptor 21 can be integrated or otherwise permanently attached to the connector 12 as a monolithic structure or can replace or be used in place of the connector 12.

In various embodiments, the end of the light cable is configured to be removably attached to a laparoscope or the connector of the lighted surgical access device. In various embodiments, the connector and/or adaptor is configured to removably connect directly to a light source. In various embodiments, the connector and/or adaptor is configured to removably connect to a light cable. In various embodiments, the connector is provided to specifically attach to a specific connection presented at the end of the light cable. In various embodiments, the connector and/or adaptor is customizable or adjustable to accommodate one or more different types of connectors or connections presented or offered at the end of the light cable. In various embodiments, the connector and/or adaptor is connectable and/or compatible with industry standard surgical light cables.

In various embodiments, the connector 12 has a snap-fit connection in which one or more adaptors, e.g., adaptor 21*a*, *b*, are arranged to snap onto an open end of the connector 12. In various embodiments, the connector 12 includes one or more O-rings or snap rings with corresponding grooves or channels configured to seal and engage the inner diameter of the adaptor to further enhance the connection between the two. In various embodiments, the connector 12 and/or adaptor 21 includes one or more flanges extending radially from the outer surface of the connector and/or adaptor to prevent or restrict the travel or extension of the adaptor or a connection or connector thereto over the connector 12 and/or adaptor 21. In various embodiments, the adaptor has similar connection type ends. For example, adaptor 21*a* has a snap fit connection on one end and a snap fit connection on the opposite end. In various embodiments, the adaptor has dissimilar connection type ends. For example, adaptor 21*b* has a snap fit connection on one end and a threaded connection on the opposite end. In various embodiments, the connector 12 is used without the adaptor 21.

In various embodiments, the adaptor is arranged to press fit over the outer surface of different types of light cables. In various embodiments, the adaptor is arranged to connect or secure the connection and/or light cable via a magnetic connection. In various embodiments, the adaptor includes a friction-based push-lock where insertion of the light cable within an opening in the adaptor and the subsequent release of the light cable connects and secure the light cable to the adaptor. In various embodiments, the adaptor is arranged to connect directly to a connection on the light box or source. In various embodiments, the adaptor comprises of clamshell-like components arranged to clamp and secure the light cable and the POF together. In various embodiments, the clamshell further comprises compressible foam or the similar materials or have different diameter tiers to fit and secure different sized or dimensioned and/or shaped light cables and/or their connectors or other intermediaries thereto. In various embodiments, the proximal end of the POF includes a preload or biasing mechanism, such as a spring or O-ring, arranged to engage an distal end of a light cable to compress, e.g., the spring, as the light cable is connected to the adaptor to bias the light cable and/or adaptor into a flush contact position. In various embodiments, the adaptor includes one or more lenses arranged to focus light from the light cable into the POF and/or connector and/or in various embodiments, the connector includes one or more lenses arranged to focus light from the adaptor into the connector and/or from the connector into the POF.

In various embodiments, the adaptor and/or connector includes a heat sink or other heat dissipation and/or insulation to reduce or minimize thermal effects that may occur due to non-flush contacts with the light cable, adaptor and/or connector. In various embodiments, the adaptor and/or connector includes an insulation sleeve arranged to reduce thermal effects and/or spread that may potentially adversely affect the user, patient, and/or the device or other surrounding device or components.

In various embodiments, the POF leader 14 communicates or transmits light from a proximal end or connector 12, in various embodiments, to the POF tail 16 and ultimately to the internal surgical site or body cavity or opening. In various embodiments, the POF leader is an elongate tube, tubular-like or cylindrical structure.

The POF leader 14, in various embodiments, is covered with heat shrink to eliminate glare, reduce bends, and/or to join or connect the connector and/or sleeve with the POF. The heat shrink or another opaque material serves as a barrier that blocks light escaping from the leader from causing glare. The heat shrink in various embodiments has a non-transparent color and/or includes or is made of non-translucent material.

In various embodiments, the POF leader 14 and/or POF tail 16 comprises a heat shrink that provides a layer of material constricting the POF and preventing sharp bends. Sharp bends in the POF can cause a substantial amount of light to be lost. To help anchor or seal the connector, adaptor and/or sleeve to the POF, in various embodiments, the heat shrink is used. It should be noted that the heat shrink eliminates glare, reduces bends, and joins the adaptor and/or connector with the POF, solving multiple problems at once. In various embodiments, the POF may be painted or coated to eliminate glare, stress releasers used to reduce bends, and/or clamps used to join or connect to the adaptor, connector or sleeve to separately or individually to reinforce the heat shrink or accomplish the task separately or individually.

In various embodiments, the POF leader 14 is configured to maintain flexibility to allow a user to manipulate the POF and avoid tissue trauma against the incision wall or interfere with the sheath of the retractor. In various embodiments, the POF leader is configured to prevent the POF from dislodging or shifting to maintain optimal light output or throughput between the light source and the POF. In various embodiments, the POF leader is configured to block light emitting from the POF until the light reaches the POF output site to thereby to maximize the illumination or reduction of delivered or communicated light at the site. In various embodiments, the POF leader includes opaque, e.g., black, film or lining that may or may not be heat shrunk that provides flexibility and light blockage. In various embodiments, select portions, e.g., the proximal and/or distal portions or ends of an opaque film, sleeve, wrap, or lining are heat shrunk onto the tube of the POF leader. In other embodiments, the POF leader is less opaque, e.g., white, with a film or lining that may or may not be heat shrunk that provides flexibility. In various embodiments, the POF leader comprises a black adhesive lined heat shrink that provides flexibility, resistance to pull force or dislodgement of the POF leader and light blockage. In various embodiments, light output may be increased by wrapping the POF leader with a reflective material before applying the heat shrink. The reflective material reflects escaping light back into the POF.

In various embodiments, the POF leader includes cuts, slits and/or scoring to act as cooling scores to reduce or dissipate some of the light energy entering the POF and prior to such energy reaching the POF tail. In various embodiments, cooling scores are provided under an opaque film, sleeve, wrap, or lining are heat shrunk onto the POF leader, e.g., a black adhesive lined heat shrink. In various embodiments, the opaque film, sleeve, wrap or lining are heat shrunk onto the POF leader, e.g., a black adhesive lined heat shrink, absorbs the light from the cooling scores and thereby allows heat energy to be dissipated across a larger surface area along the POF and not concentrated at the POF tail and/or the distal end or distal most end of the POF tail 16.

Figure 15:
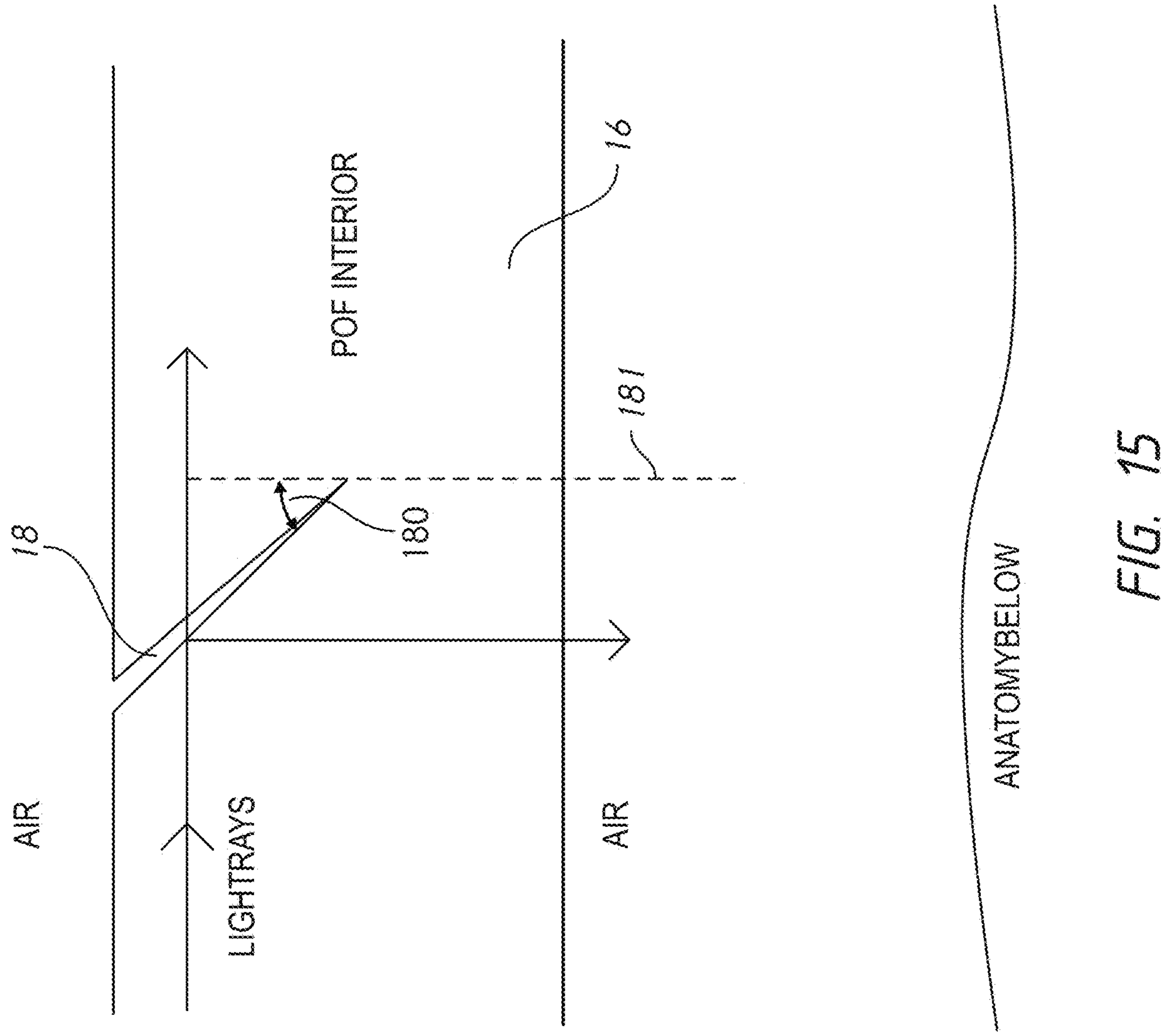
FIG. 15 is a graphical representation of a plastic optical fiber exemplifying a cut relative to incoming light and an internal surgical site in accordance with various embodiments of the present invention.
Figure 16:
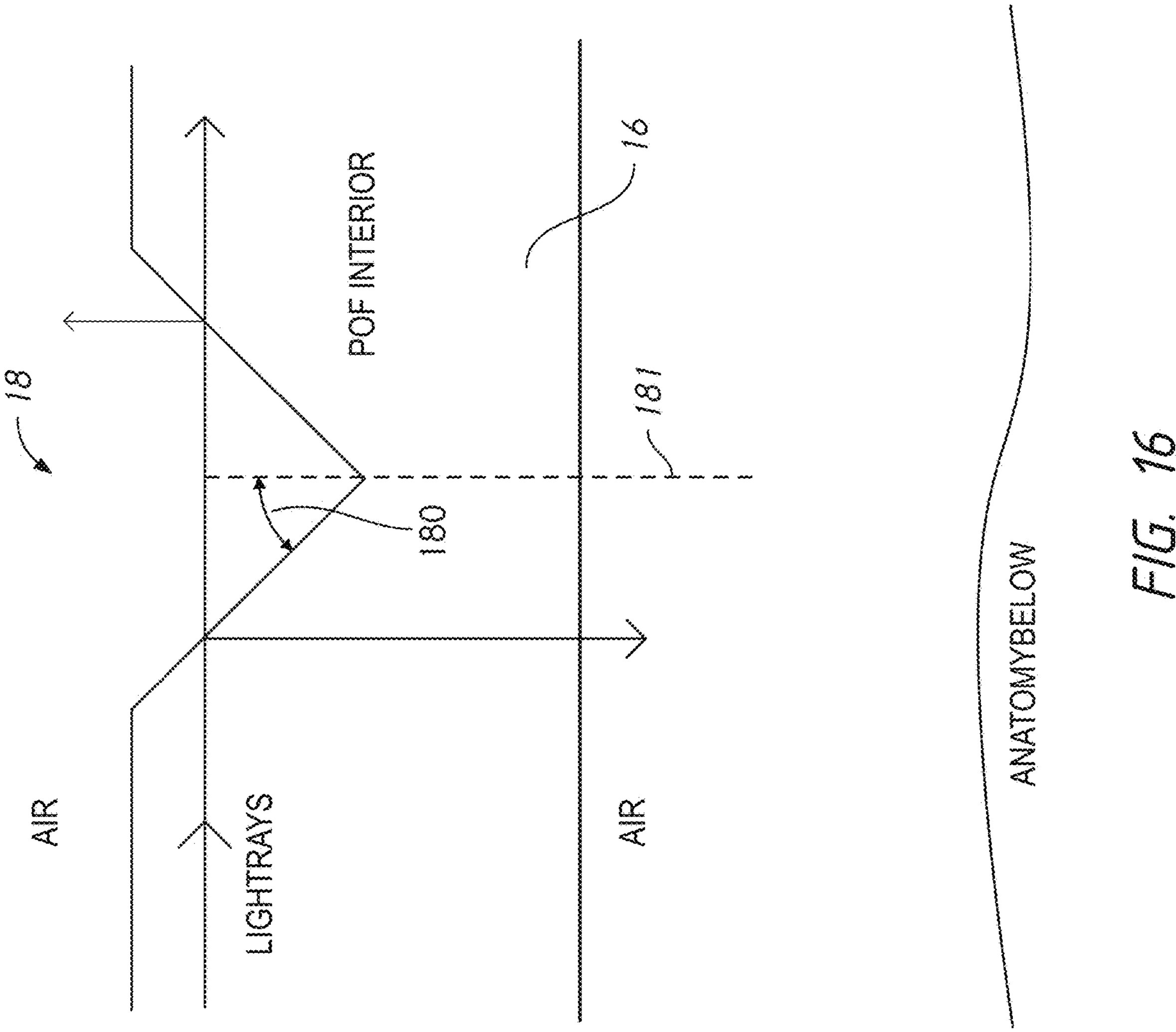
FIG. 16 is a graphical representation of a plastic optical fiber exemplifying a cut relative to incoming light and an internal surgical site in accordance with various embodiments of the present invention.
Figure 18:
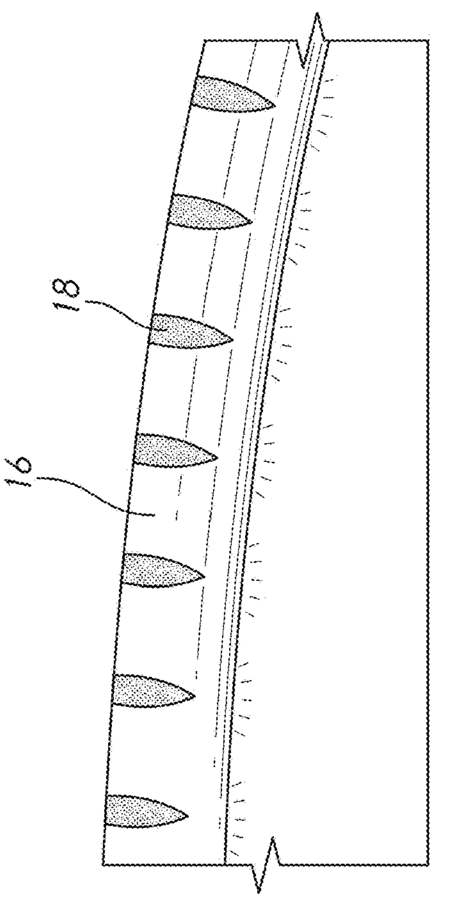
FIG. 18 is a top perspective view of a plurality of cuts or scoring in a plastic optical fiber in accordance with various embodiments of the present invention.
Figure 17:
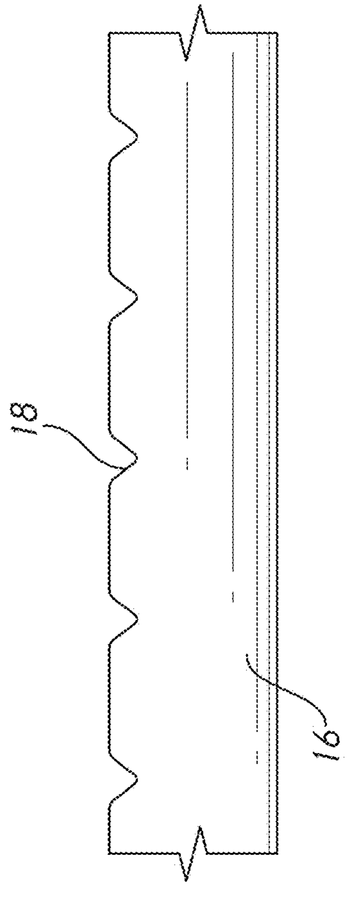
FIG. 17 is a side view of a plurality of cuts or scoring in a plastic optical fiber in accordance with various embodiments of the present invention.

In various embodiments, the POF tail 16 is configured to lie or be placed inside the surgical site. In various embodiments, the POF tail is an elongate tube or a tubular-like or cylindrical structure. In various embodiments, the POF tail comprises one or more cuts, scoring or indentations 18. The cuts 18 in various embodiments are angled at a predetermined or predefined angle, e.g., at or around 45 degrees, to ensure total internal reflection, for more than half of the light that encounters the cuts. In various embodiment, the scoring or cuts are angled between 42 to 45 degrees, e.g., angle 180 relative to axis 181 as shown in FIGS. 15-16. The light refracts out of the POF once it reaches the other side of the POF because the angle between the light rays and surface of the POF are large enough that light escapes instead of bouncing inside the POF. Reflecting light to the other side of the POF is beneficial because the cylindrical POF wall helps diffuse light. The cuts are positioned so that the refracted light is directed to the internal anatomy.

In various embodiments, the frequency or the number of the cuts 18 are predetermined or predefined to create an even extraction and distribution of light near the distal end of the sheath and/or at the internal surgical site. Each cut extracts light and decreases the amount of light traveling through the POF thus resulting in dimmer subsequent cuts. To compensate or account for the dimness, the frequency/amount of the cuts in various embodiments are predetermined such that light extraction is uniform throughout. In various embodiments, the one or more cuts are predetermined or predefined in spacing or positioning to create an even extraction and distribution of light near the distal end of the sheath and/or at the internal surgical site.

The cuts in various embodiments are on the surface or punched through the POF. Circular holes through the POF can achieve similar results as cuts. In various embodiments, the POF is scored to increase the brightness and/or light output at the surgical site about 10 times greater than bare POF or POF unscored. Additionally or alternatively, the POF is scored to reduce the power required to generate a desired light output and/or brightness and in various embodiments reduces power required to about 50 to 60 percent than that required by bare POF or POF unscored.

In various embodiments, the scoring of the POF 11 can vary in frequency and/or depth to vary the light output, focus and/or direction of the light at the surgical site, e.g., highlighting or focusing on certain portions relative to the orientation of the retractor and the POF attached thereto.

As shown, for example, at least in FIGS. 21A-21D, the distal end 17 of the POF 11 may have a predefined or predetermined end profile, covering and/or cap. In various embodiments, the distal end 17 of the POF 11 has a flat end, profile or shape, e.g., a flat end 17*a*, and/or a cap, cover or lens with a flat end, shape or profile. The flat end 17*a* is configured to direct light from POF 11 directly in-line or longitudinally out the distal end 17 of the POF along a center axis of the POF. As such, the light of the POF exits unobstructed and is not reflected back into the POF. In various embodiments, the distal end 17 of the POF 11 has an angled end, shape or profile, e.g., angled end 17*d*, and/or a cap, cover or lens with an angled or slanted end, shape or profile. The angled end 17*d* is configured to direct light from POF 11 orthogonally or angled relative to a center or longitudinal axis of the POF and/or offset or parallel to the center axis of the POF.

In various embodiments, the end profile of the POF 11 is tapered or rounded to refract light radially. In various embodiments, the distal end 17 of the POF 11 has a tapered or rounded end, profile or shape and/or a cap, cover or lens with a tapered or rounded end, shape or profile, e.g., a tapered end 17*b* or rounded end 17*c*. For example, in various embodiments, instead of the light escaping parallel to the POF 11 it is distributed radially and thus illuminating the internal anatomy. Inside the POF 11, in various embodiments, light is traveling at +/−25 degrees to the POF center axis. In order to extract all of that light radially the end profile is tapered to +/−23 degrees. In various embodiments, a tapered profile of the POF extracts the light radially. In various embodiments, the distal portion or end of the POF has a profile or shape that is different from a distal end or portion of the cap, cover or lens of the POF. In various embodiments, the distal end 17 of the POF 11 has an end, profile or shape and/or a cap, cover or lens with an end, shape or profile of a different geometry other than flat, such as round or a prism, to direct or diffuse light for enhanced illumination, minimize light interference and/or reduce heat or thermal energy.

Figure 5:
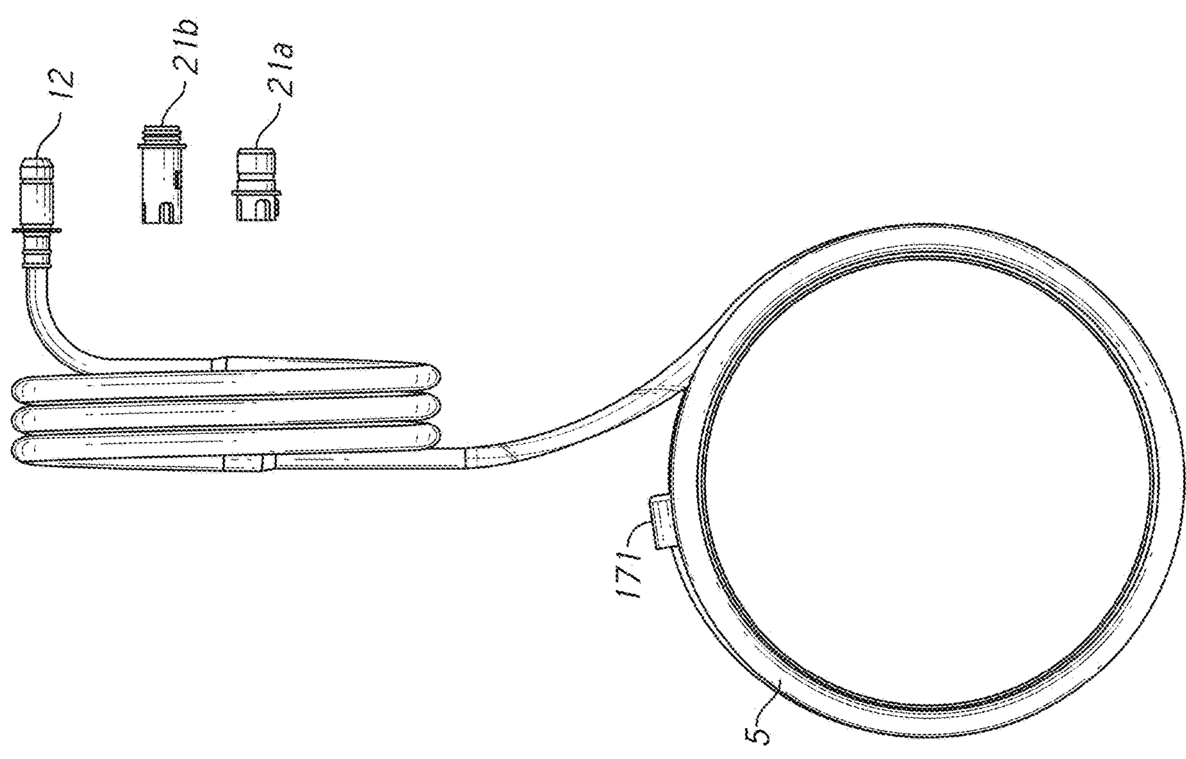
FIG. 5 is a top view of a lighted surgical access system in accordance with various embodiments of the present invention.
Figure 6:
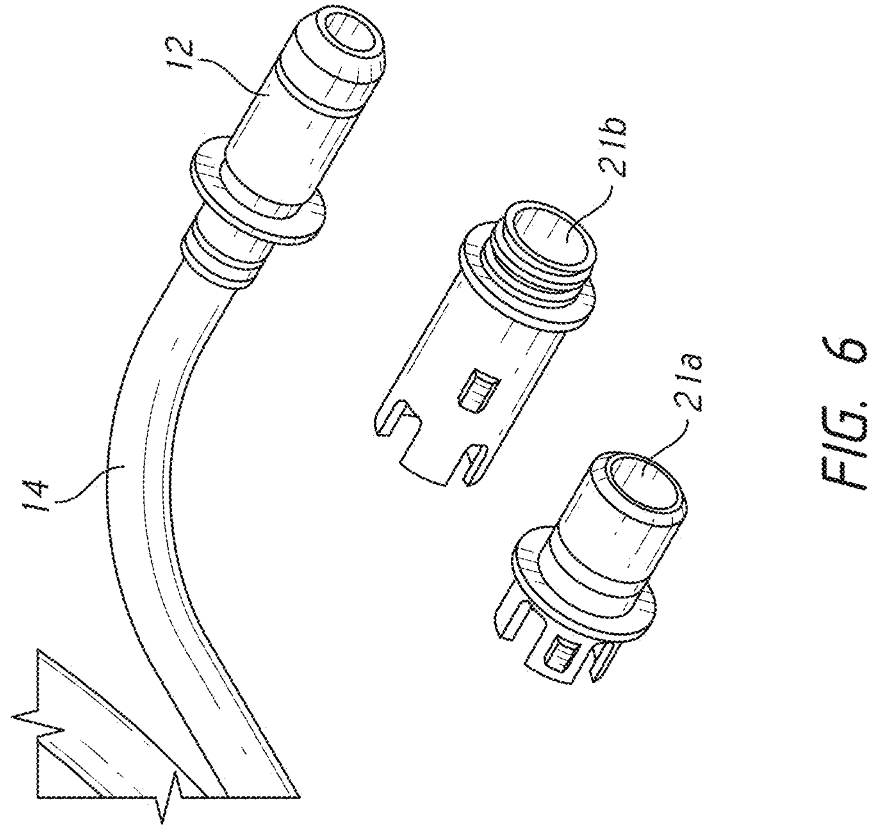
FIG. 6 is a perspective view of portions of a lighted surgical access system in accordance with various embodiments of the present invention.
Figure 7:
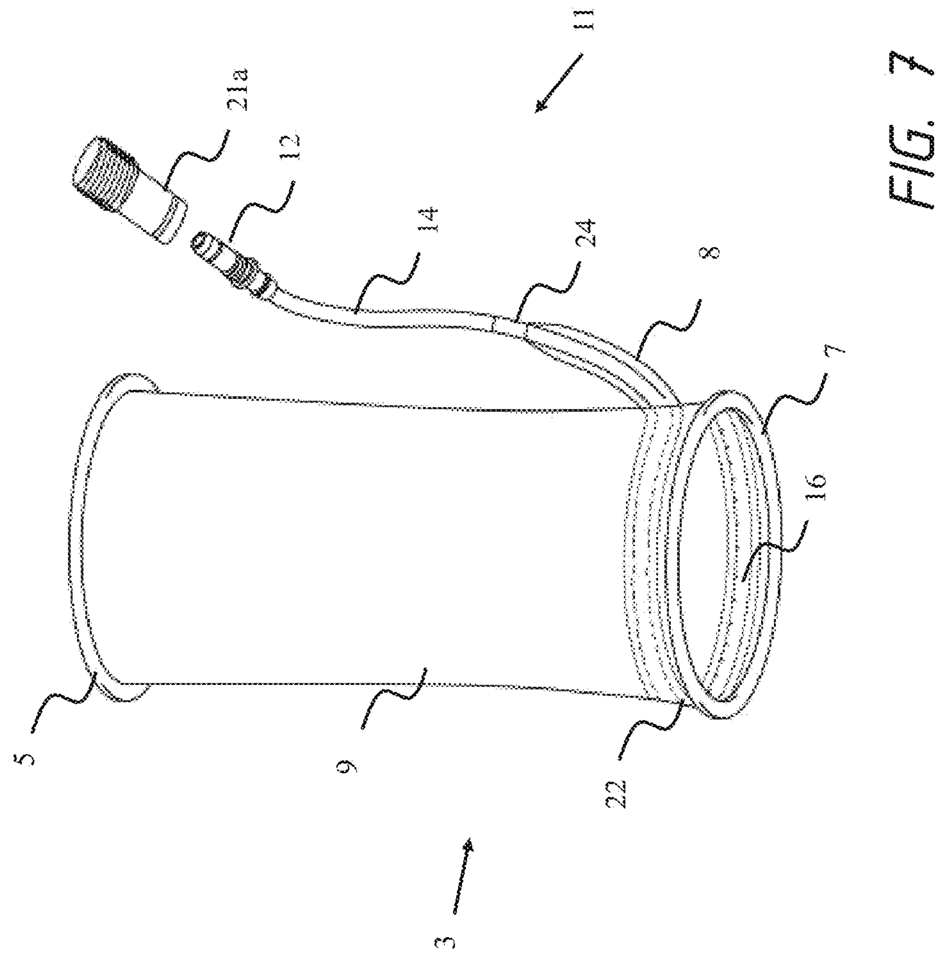
FIG. 7 is a perspective view of a lighted surgical access system in accordance with various embodiments of the present invention.
Figure 8:
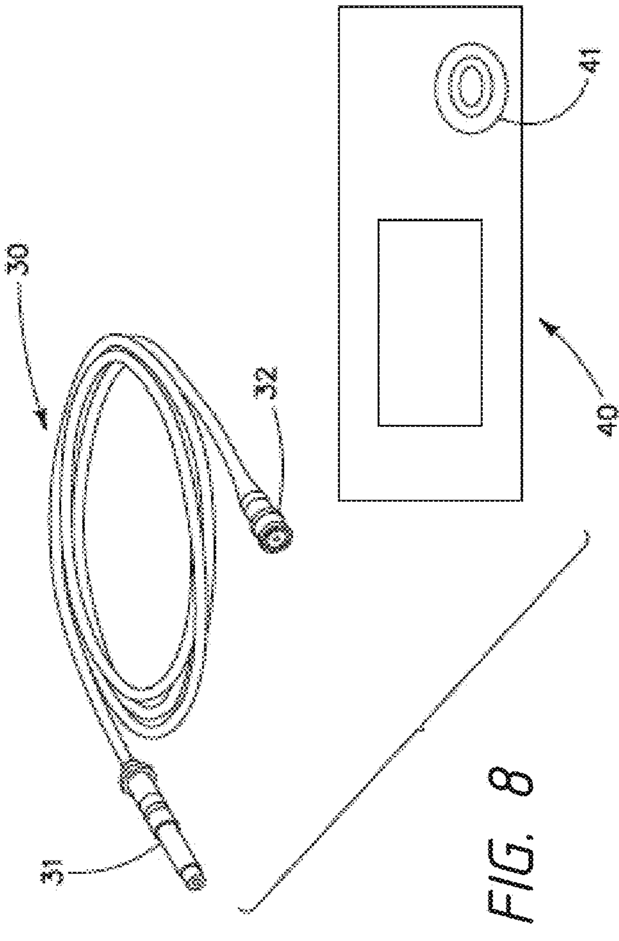
FIGS. 8-11 are perspective views of portions of a lighted surgical access system in accordance with various embodiments of the present invention.
Figure 9:
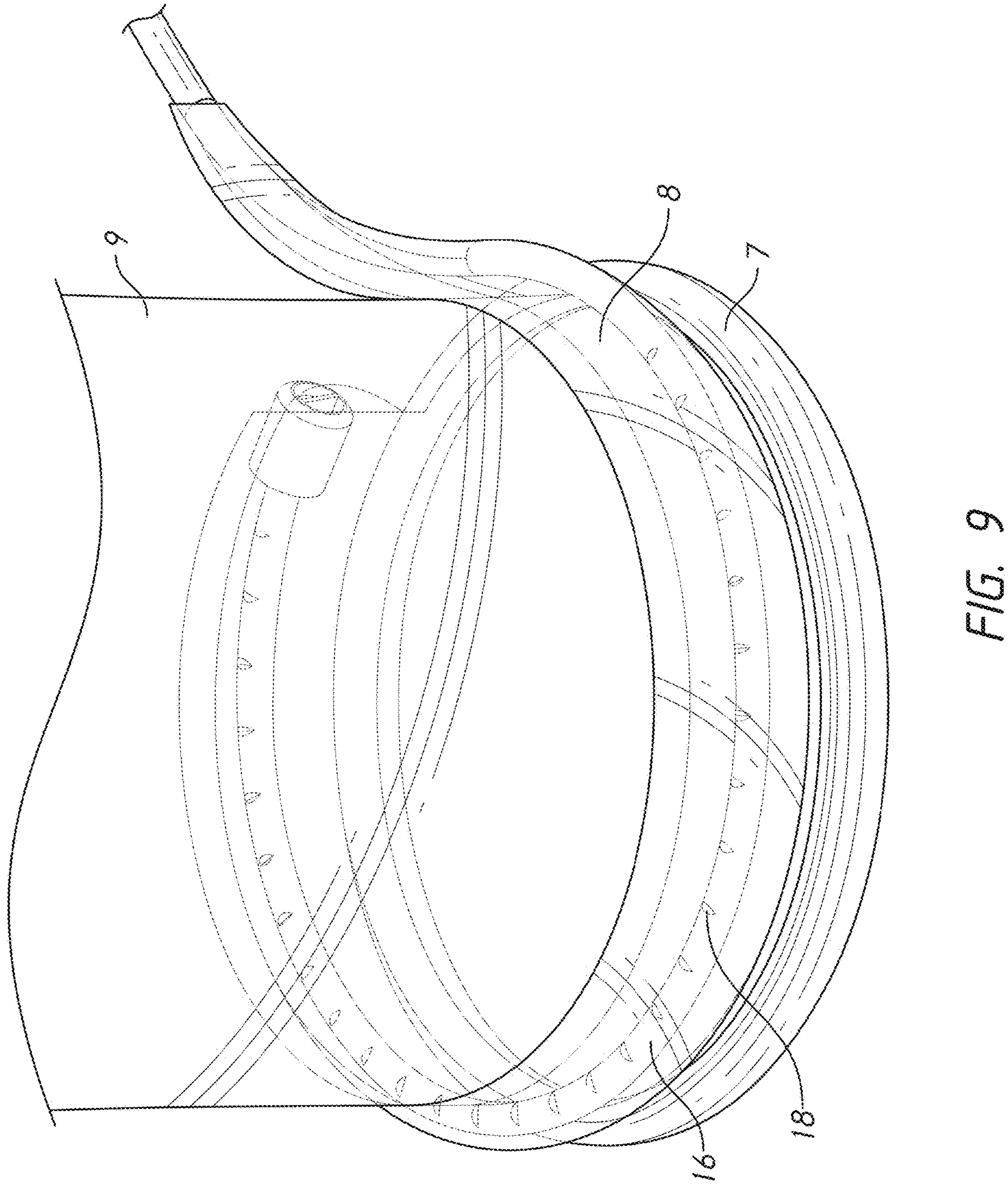
Figure 10:
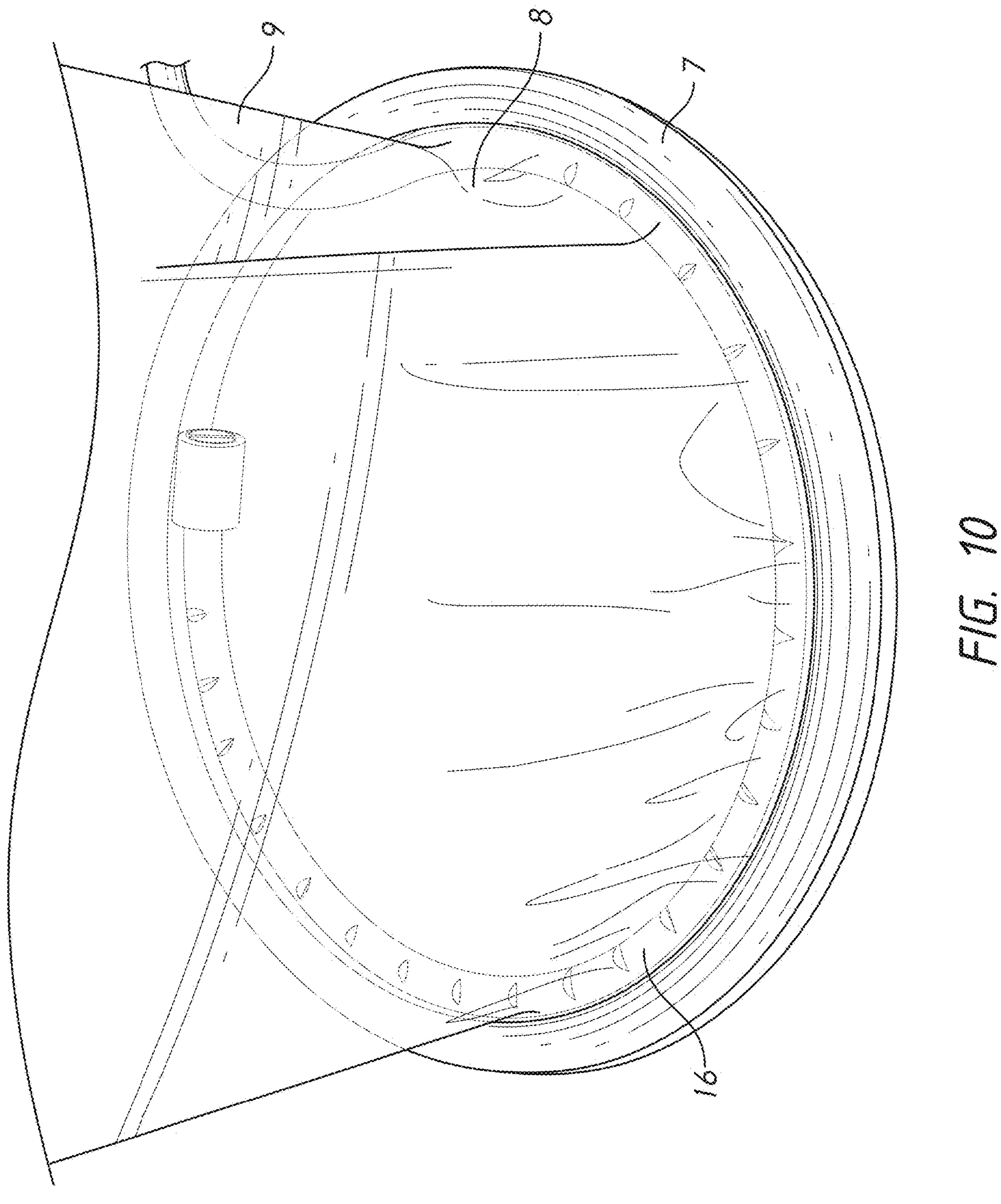
Figure 11:
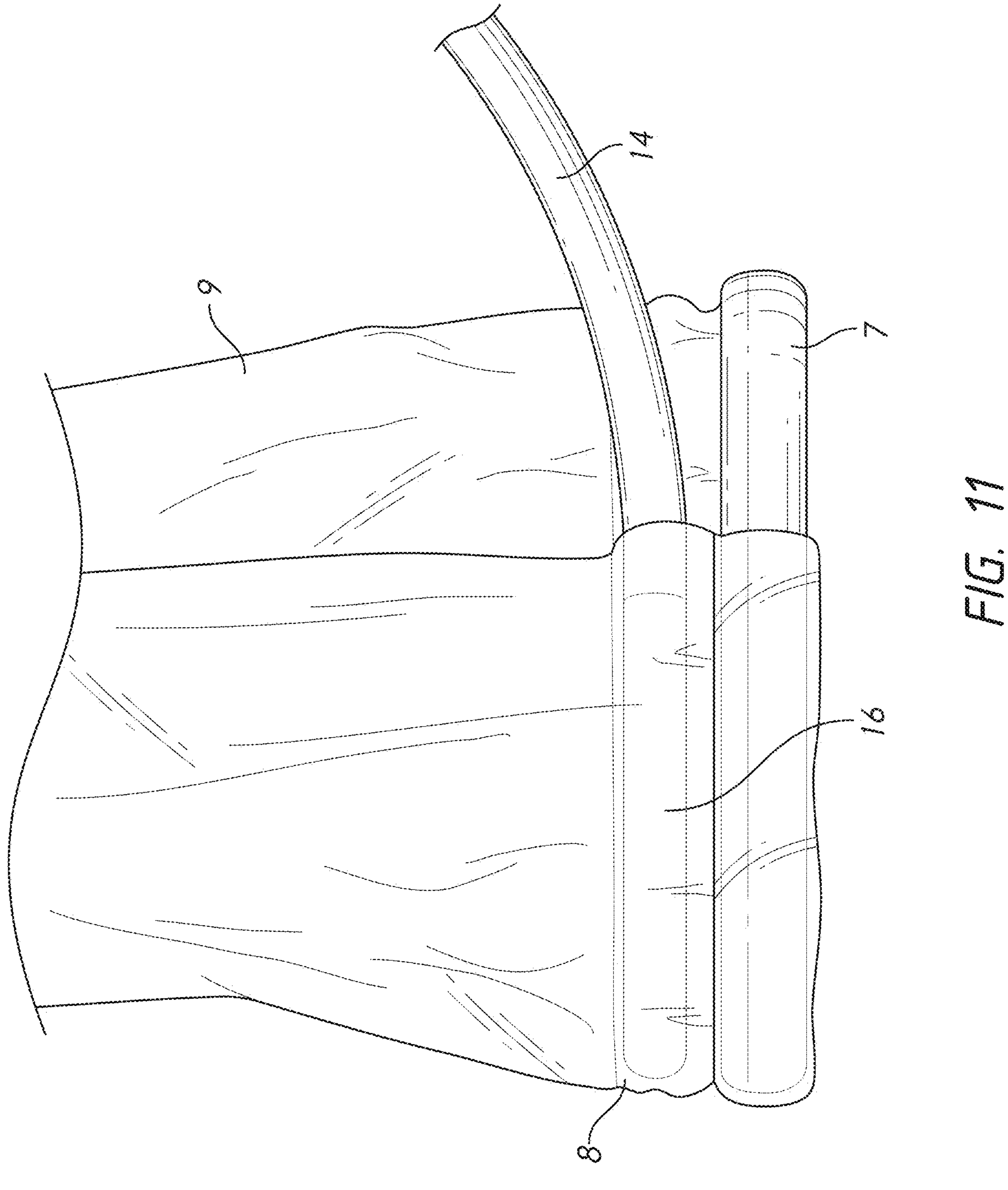
Figure 12:
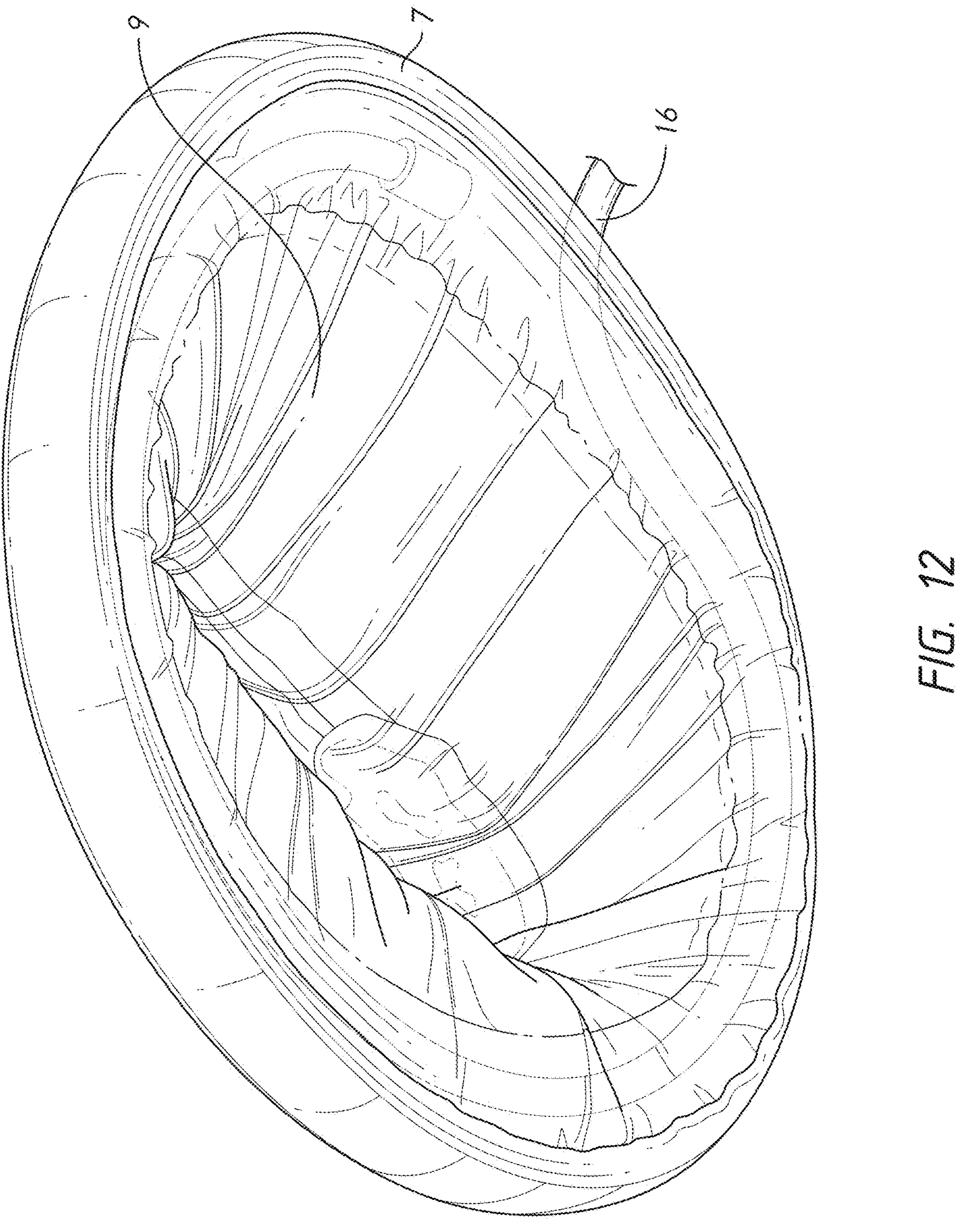
FIG. 12 is a bottom perspective view of portions of an activated lighted surgical access system within and illuminating an internal surgical site in accordance with various embodiments of the present invention.
Figure 13:
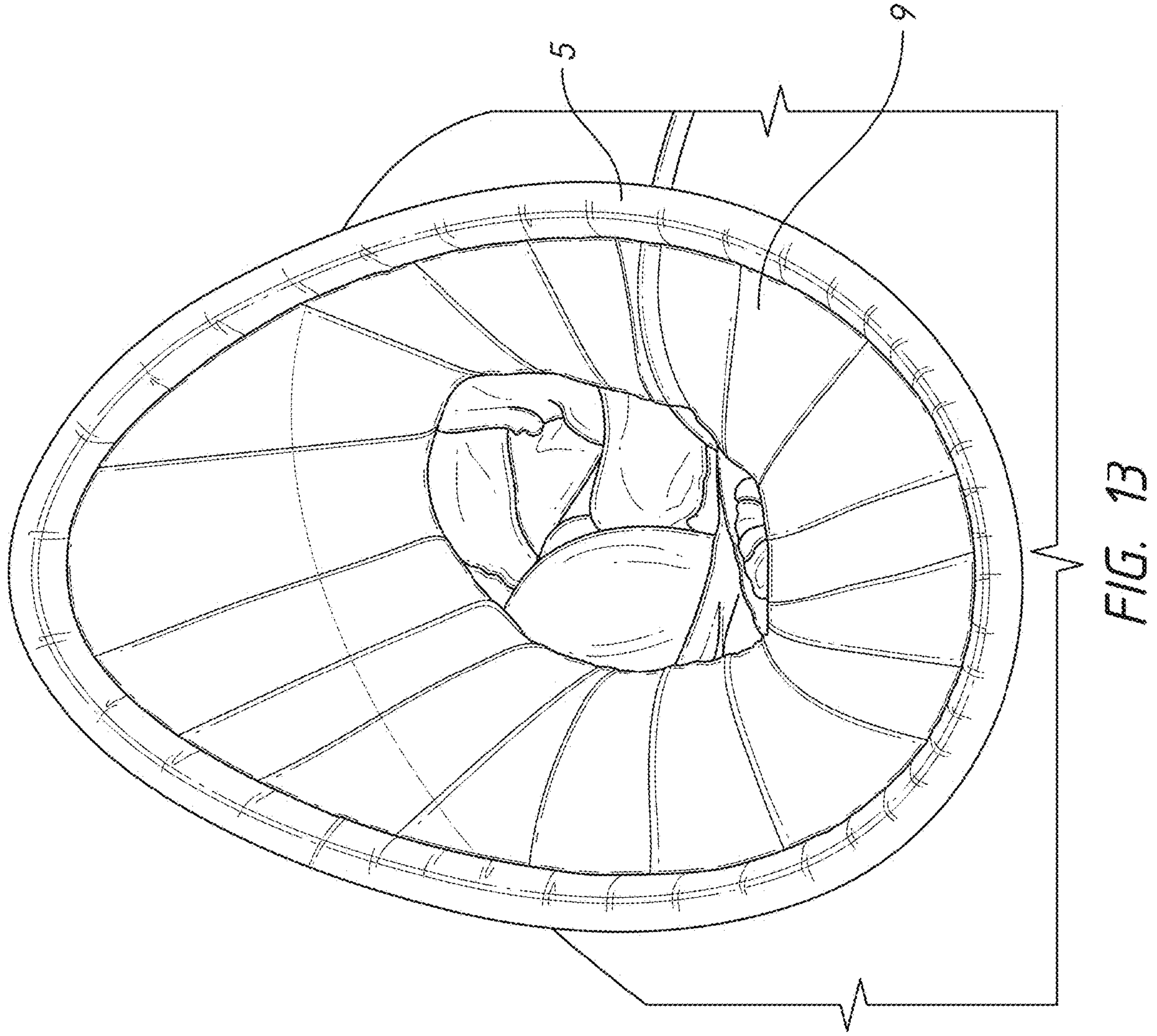
FIG. 13 is a top view of portions of an activated lighted surgical access system within and illuminating an internal surgical site in accordance with various embodiments of the present invention.
Figure 14:
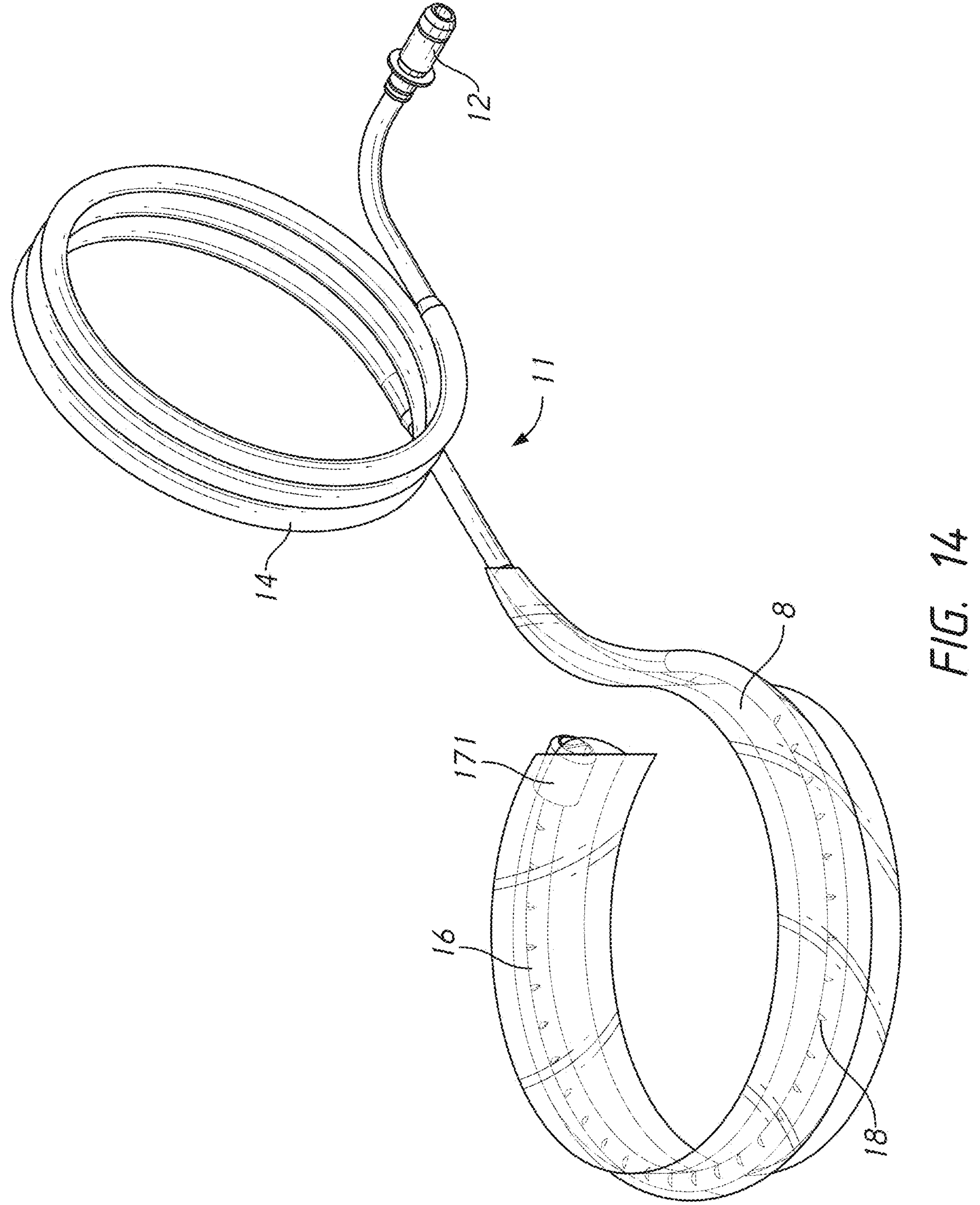
FIG. 14 is a perspective view of portions of a lighted surgical access system in accordance with various embodiments of the present invention.

In various embodiments, the distal end 17 of the POF 11 has a predetermined profile or shape and/or a cap, cover or lens with a predetermined shape or profile to help diffuse or redirect light to the internal anatomy and distribute light/thermal energy more evenly. In various embodiments, the distal end 17 of the POF 11 is coated, covered or otherwise configured to help diffuse or redirect energy or light exiting out the distal portion or end of the POF 11. In various embodiments, the cap, cover or lens is integrated into the distal portion or end 17 of the POF 11 forming a monolithic structure. In various embodiments, the cap, cover, or lens, e.g., cap 171 as shown in FIGS. 5 and 14, is friction-fit, adhered or otherwise attached to the distal portion or end 17 of the POF 11. In various embodiments, the cap, cover or lens has an inner diameter matching or somewhat larger than the outer diameter of the distal portion or end of the POF to friction-fit or otherwise attach to the distal portion or end of the POF. In various embodiments, the cap, cover or lens has an outer diameter larger than the outer diameter of the distal portion or end of the POF. In various embodiments, the cap, cover or lens includes an inner concentric tube or cylinder and/or one or more protrusions configured to attached or connect an outer surface of the inner tube, cylinder or protrusion to an inner surface of the distal portion or end of the POF to further secure the cap, cover or lens to the distal portion or end of the POF. In various embodiments, the cap, cover or lens has one or more indents or cavities along or within an outer or end surface of the cap, cover or lens to facilitate attachment and/or removal of the cap, cover or lens and/or to diffuse or direct energy or light of the POF.

In various embodiments, the cap, cover or lens includes a reflective film, coating or lining to help reflect some of the light energy back into the POF tail which in return is reflected out into the body cavity and/or increase light intensity rather than being fully absorbed by the cap, cover or lens. In various embodiments, a disc of mirror-like reflective film may be placed on, e.g., inside, the cap, cover or lens or adhered to the end portion of the POF tail with the disc reflective film configured to reflect light back into the POF, brightening the light emitted into the body cavity and reducing heat absorbed by the cap, cover, lens or end portion of the POF tail, reducing or lowering temperature experienced by the same. In various embodiments, a cap or cover is positioned on a distal most end of the POF tail both of which are placed within the sleeve and, in various embodiments, the cap, sleeve and/or sheath insulate the outside or surrounding area from heat being generated by the light at the end of the POF tail. In various embodiments, the cap is arranged to minimize the temperature on the outside of the cap. For example, the cap has an outer shell creating an insulating air gap between the core or inner portion of the distal end of the POF tail and/or an inner shell or portion of the cap connected thereto. In various embodiments, the POF and/or the POF tail and/or the cap, cover or lens has a wall thickness, coating, covering and/or material that is configured to prevent the temperature of the POF tail and/or cap, cover or lens from exceeding a predetermined temperature, e.g., 43 degrees C., or range, e.g., 40-45 degrees C. or less than or equal to 43 degrees C.

In various embodiments, the lighted surgical access system includes two thermoplastic polyurethane (TPU) inner and outer rings, TPU film that forms a sheath between the rings, a plastic optical fiber (POF) made from methyl methacrylate, polyolefin heat shrink tubing that covers a portion of the POF, and/or connectors and/or adaptors for compatibility with industry standard surgical light cables.

In accordance with various embodiments, a lighted surgical access device or system is provided to eliminate the drawbacks associated with current surgical lighting technologies. In accordance with various embodiments, the lighted surgical access device or system provides illumination in the internal surgical site, body cavity, incision, or opening while providing 360 degrees of hands-free retraction and/or protection. The lighted surgical access device or system is thus configured to provide circumferential, atraumatic retraction as well as illumination of the internal surgical site, body cavity, incision, or opening to gain maximum exposure within the patient's body cavity, incision and/or opening.

In various embodiments, the lighted surgical access system positions the lighting element underneath the incision or patient opening, which eliminates the problems of glare and/or shadows around the incision and insufficient light entering through small incisions or openings. In various embodiments, the POF is positioned and/or mounted to the sheath above the inner ring thereby avoiding or reducing obstruction by the inner ring, not obstructing the ability of the inner ring to anchor within the patient's cavity and/or not reducing the flexibility of the inner ring in placement through the patient's opening and/or within the patient's cavity, yet aligning light output into the internal surgical site.

In various embodiments, a portion of the POF configured to sit below the incision or patient opening has scoring or cuts to help disperse light from the POF and illuminate the internal surgical site or space, body cavity, incision, or opening. The POF leader or portions thereof of the POF that feeds out through the incision or opening, in various embodiments, is shielded to block light from escaping and terminates with a connector and/or an adaptor to connect to standard surgical lighting units or sources. Positioned under the incision or opening, the light emitting portion of the lighted surgical access system is unable to produce glare on the top of the incision or opening, which preserves the visual contrast of the internal surgical site or space. In addition, since the light is carried into the incision or opening by a POF and then dispersed, the amount of light that can illuminate the surgical space is not limited by the size of the incision or opening.

In various embodiments, the hoop or semi-circular shape of the POF contributes to the lighting effectiveness of the lighted surgical access device or system. In various embodiments, the exposed portion of the plastic optical fiber is mounted circumferentially around the sheath, following the path or outline of the sheath or the inner ring, and light is emitted evenly around the circumference of the sheath or inner ring. Therefore, the light emitted from the system is evenly distributed and/or omnidirectional rather than originating from a single point, which eliminates the problem of shadows being cast in the surgical field. For instance, if the surgeon's hand or an instrument is inserted in the incision or opening and thereby blocking the light or portions thereof from one side of the ring, the other half of the ring will still be illuminating the site, preventing a disruptive shadow. The evenly distributed and/or omnidirectional nature of the light also solves the problems of frequent repositioning (e.g., typically necessary for overhead lamps) and keeping the light pointed in the right direction (e.g., typically problematic for headlamps). With the light positioned in the incision or opening and able to come or be dispersed from all angles, the need to adjust its positioning or angle to achieve sufficient lighting, even when the patient needs to be repositioned, is minimized or eliminated.

With the POF integrated or otherwise attached to the self-retaining retractor allows the lighted surgical access device to be completely hands-free in use. This solves the problem and/or the inconvenience of other lighted retractors, which require a member of the surgical team to continuously hold the retractor in place. Operationally, in accordance with various embodiments, the lighted surgical access device is placed in the incision by squeezing the inner ring and inserting it through the incision or opening, where it then expands and anchors. The outer ring is flipped down to tension the sheath and retract the incision. At this point, the lighted surgical access device or system requires no further adjustment and will continue to retract the incision or opening hands-free. With the POF mounted or otherwise attached to the sheath above or spaced away from the inner ring or distal most portion or end of the sheath, the addition of the POF does not change or otherwise interfere with the retraction operation or procedure and/or anchoring of the inner ring, and the lighted surgical access device or system can be used hands-free after initial positioning. In various embodiments, with the POF mounted or otherwise attached to the sheath above or spaced away from the inner ring or distal most portion or end of the sheath, light interference by the inner ring or distal portions of the sheath can be avoided or eliminated and/or positioning of the POF can be eased and/or optimized.

In various embodiments, the POF is one or more plastic optical fibers. In various embodiments, a bundle of plastic optical fibers is used, enhancing flexibility of the POF, and, in various embodiments have equal diameters. In various embodiments, the POF is a plurality of plastic optical fibers that when bundled together delimit a circle or cylinder having about a 5 mm diameter. In various embodiments, the plurality of plastic optical fibers combines at a junction between the POF leader and the POF tail at or proximate the sheath 9, sleeve 8 and/or the inner ring 5. In various embodiments, a plurality of smaller POF fibers from the POF leader terminate at different points along or proximate the inner ring 5 and/or the distal end of the sheath to disperse light at those selected points. In various embodiments, the POF comprises a plurality of plastic optical fibers having different lengths and/or diameters to disperse light at different points and/or adjust flexibility of the POF at different portions of the POF. In various embodiments, the POF is a single plastic optical fiber having about a 5 mm diameter. In various embodiments, the POF has a diameter that is equal or greater than the diameter of the light cable. In various embodiments, the POF is elongate and tubular and in various embodiments, comprises one or more plastic optical fibers that are elongate and tubular. In various embodiments, the POF leader or portions thereof aligned with a patient's opening or incision has a thinned, reduced or smaller profile, e.g., having a oval, rectangular shape or the like, preventing obstruction and/or interference with the retractor and/or the patient's body, opening and/or an incision.

In various embodiments, the POF or portions thereof is or includes an end-glow fiber to reduce light loss. In various embodiments, the POF comprises different types of plastic optical fibers. For example, in accordance with various embodiments, the POF leader comprises an end-glow POF and transitions to a side-glow POF at a predetermined junction at or proximal to the sheath. In various embodiments, the POF leader comprises an end-glow POF and the POF tail comprises a side-glow POF. In various embodiments, a coupler, e.g., a T-shaped coupler, is provided in that the POF leader terminates at or proximate the inner ring with the T-shaped coupler positioned and connecting between the POF leader and one or more side-glow POFs, e.g., the POF tail comprises one or more side-glow POFs. In various embodiments, the POF or portions thereof are molded to an arcuate or circular shape having one or more bubbles embedded therein to disperse light away from the outer ring and towards the internal surgical site or area of interest.

In various embodiments, the POF and/or sleeve is configured to not exceed a predetermined temperature, e.g., 40-45 degrees C. or 43 degrees C. In various embodiments, the POF and/or sleeve so configured includes one or more layers, coatings, films or thermal or heat dissipating or reducing insulation. In various embodiments, an additional or second sleeve is provided and attached to the sheath. The second sleeve encases or covers the POF leader. In various embodiments, the second sleeve is orientated vertically or diagonally relative to a longitudinal axis of the sheath and its access channel. In various embodiments, the second sleeve is oriented in a transverse direction relative to the sleeve containing the POF tail. In various embodiments, the second sleeve and the sleeve containing the POF tail are combined or monolithically formed to provide a single structured sleeve. In various embodiments, all or portions of the POF and/or sleeve includes or is integrated with a reflective film, coating or cover to reflect light back into the POF to reduce light loss. In various embodiments, a cable-management device or system is attached or integrated with the POF to regulate, control or dispense a desired length of the POF for operational use while any excess remains managed, e.g., coiled or wrapped, to prevent obstruction of an excess portion of the POF.

In operation, surgical retraction is achieved by first compressing and inserting the inner ring into the incision or opening and seating it beneath the desired anchoring tissue. The outer ring is then flipped or rolled by the user, which tensions the sheath and applies outward pressure to the wound or opening, effectively retracting the tissue. Placement of the POF being proximate and/or spaced from the inner ring or distal most portion of the sheath places the POF within the internal surgical site and/or the access channel, beneath the anchoring tissue and/or the incision or opening. The lighted surgical access system illuminates the internal surgical site and/or the access channel by transmitting light through the POF, which is sealed onto the sheath above the inner ring, and spans from within the incision or opening to outside the sterile field. Light is provided from a surgical light source and is transferred through a surgical light cable. The light cable is connected to one of the adaptors of the system. Once the surgical procedure is completed or as desired, the user can disconnect the light cable from the adaptor and/or connector and extract the lighted surgical access device from the surgical site.

In various embodiments, the POF is kept separated from the sheath and subsequently attached to the sheath for operational use. In various embodiment, the POF is incorporated, fitted or placed into the sleeve of the sheath at the time of the procedure or in anticipation of the surgical procedure for operational use. In various embodiment, the sheath comprises a pocket in which the POF is incorporated or placed into the sheath at the time of the procedure or in anticipation of the surgical procedure for operational use. In various embodiments, the POF with or without the sleeve is entrapped between the inner ring and the sheath by wrapping the sheath around the POF by, for example, flipping the inner ring attached to the sheath over and around the POF. In various embodiments, a cushion or impact resistant barrier is provided such as rubber or elastomeric cushion attached or otherwise connected to the POF, sheath and/or sleeve to insulate or protect the body or surgical opening from manipulations or pressure exerted by the POF during operational use. In various embodiments, the cushion or impact resistant barrier is disposed between the POF tail, leader and/or both and the body opening and/or incision. In various embodiments, the POF tail, leader or both is disposed between the cushion and/or impact resistant barrier and/or the sheath and/or sleeve.

In various embodiments, the lighted surgical access system may include a retractor and a POF connected to or otherwise attached to the retractor. In various embodiments, the lighted surgical access system may include a light source, a retractor and a POF connected to the retractor and the light source. In various embodiments, the POF is removably connected to the light source and/or the retractor. In various embodiments, the lighted surgical access system can include a light cable connecting the light source to the POF. In various embodiments, the lighted surgical access system may include a surgical access device and a POF connected to or otherwise attached to the surgical access device. In various embodiments, the surgical access device may be or include a retractor, a cannula, a trocar or the like providing access or a channel or pathway into a patient's body cavity and/or in various embodiments may be flexible being able to bend and/or allow tissue or the like to deform or compress portions thereof.

In various embodiments, the lighted surgical access system may include a retractor that is adjustable in length to accommodate different patient anatomy and/or 360 degrees of hands-free protection and/or retraction of the opening in the patient. In various embodiments, the retractor may not include an outer ring, an inner ring or both. In various embodiments, the lighted surgical access system may comprise a surgical access device, a POF and/or a light source. In various embodiments, the lighted surgical access system comprises a POF. In various embodiments, the POF is spaced and separated from the inner ring and/or the distal most portion, component or end of the sheath or surgical access device. In various embodiments, the POF is fixed to the sheath or otherwise confined longitudinally or lengthwise along or relative to the sheath. In various embodiments, one or more POFs may be attached to the sheath with one or more extending circumferentially or along portions thereof around the sheath. In various embodiments, the inner ring or support or portions thereof in its entirety or one or more portions thereof is made of one or more POFs, e.g., a molded POF and/or side-glow POFs. As such, in various embodiments, one or more POFs, as described throughout the application, can be used in lieu of or to act as an inner ring. In various embodiments, the sheath or portions thereof is arranged to act as a light curtain carrying light under the body wall or patient opening to or at the internal surgical site. In various embodiments, a skirt, drape, and/or a second sheath is attached and/or extends from the distal end of the sheath and/or the inner ring to act as a light curtain to carry light under the body wall or patient opening to or at the internal surgical site.

In various embodiments, the POF comprises a POF leader and/or a POF tail. In various embodiments, the light cable and/or intermediaries thereto is directly connected to the POF tail, e.g., the POF leader is removed. In various embodiments, the POF includes a core and a cladding surrounding or encasing the core. In various embodiments, the POF outer cladding layer is modified, such as added surface roughness, to enhance light scattering. In various embodiment, the outer cladding layer is removed or portions thereof, e.g., exposing one or more sections of the core of one or more portions of the POF, e.g., the POF tail or portions thereof, under the incision or internal surgical site of interest.

In various embodiments, the POF and/or the POF tail includes one or more cuts, protrusions, projections or other deflection and/or reflection points, portions or area are shaped, sized or otherwise dimensioned to adjust light scattering of the POF. In various embodiments, the POF and/or the POF tail includes one or more cuts, protrusions, projections or other deflection and/or reflection points, portions or area to partially direct light in one or more specific directions. In various embodiments, a specific direction is towards an internal surgical site or area of interest and/or away from or opposite that of outside the patient or outer portion of the surgical access system. The one or more cuts, protrusions, projections or other deflection and/or reflection points, portions or area, in various embodiments, allow or permit the incoming light to also travel along any remainder or further along portions of the POF, opposite the incoming light travel. In various embodiments, the one or more cuts, protrusions, projections or other deflection and/or reflection points, portions or area are holes, channels, grooves, apertures or the like are angled, e.g., normal or at 45 degrees or less relative to the POF or light cable. In various embodiments, the POF and/or the POF tail includes one or more cuts, protrusions, projections or other deflection and/or reflection points, portions or area that are molded or otherwise preformed with predetermined shapes, sizes and/or dimensions to adjust or provide optimal scattering or dispersion of light. In various embodiments, the POF and/or the POF tail includes one or more cuts, protrusions, projections or other deflection and/or reflection points, portions or area that are above or on a side away from the inner ring and/or an internal surgical site or area of interest. In various embodiments, the light travels encountering other deflection, reflection or refraction points or areas and/or ultimately to the POF's terminal end. In various embodiments, the POF's terminal end comprises a specific profile and/or end cap or cover that deflections, reflections or retractions the incoming light in one or more specific directions, including allowing the incoming light to proceed uninterrupted upon exiting the terminal end of the POF, as provided by the end profile or cap. In various embodiments, the POF comprises a connector, a POF leader, a POF tail, an end cap and/or any combination thereof.

The above description is provided to enable any person skilled in the art to make and use the devices or systems and perform the methods described herein and sets forth the best modes contemplated by the inventors of carrying out their inventions. Various modifications, however, will remain apparent to those skilled in the art. It is contemplated that these modifications are within the scope of the present disclosure. Different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth.

Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments of the present invention should be considered in all respects as illustrative and not restrictive.

The invention claimed is:

1. A lighted surgical access system to illuminate internally a body cavity comprising:

an outer ring;

an inner ring;

a sheath having a proximal end connected to the outer ring and a distal end connected the inner ring, the sheath delimiting an access channel extending from the outer ring to the inner ring;

a plastic optical fiber (POF) comprising a POF leader being a proximal portion of the POF and a POF tail being a distal portion of the POF, the POF leader extending beyond the outer ring and connectable to a light source; and a sleeve connected to a distal portion of the sheath and spaced from the inner ring, the sleeve extending radially around the distal portion of the sheath and the POF tail being positioned within the sleeve.

2. The lighted surgical access system of claim 1 wherein the POF tail comprises a plurality of cuts.

3. The lighted surgical access system of claim 2 wherein the plurality of cuts are disposed on a side of the POF tail that faces away from the inner ring and are angled.

4. The lighted surgical access system of claim 2 wherein the POF tail further comprises a non-transparent material covering a portion of the POF tail.

5. The lighted surgical access system of claim 4 wherein the POF tail further comprises a reflective material disposed between the non-transparent material and the plurality of cuts.

6. The lighted surgical access system of claim 1 further comprising a non-transparent material covering the POF leader.

7. The lighted surgical access system of claim 6 wherein the POF leader further comprises a reflective material disposed between the non-transparent material and the POF leader.

8. The lighted surgical access system of claim 6 wherein the POF leader comprises a plurality of cuts.

9. The lighted surgical access system of claim 1 further comprising a reflective material positioned within the sleeve.

10. The lighted surgical access system of claim 1 wherein the sheath has an inner surface and an outer surface, the sleeve being connected to the outer surface of the sheath and further comprising a reflective material positioned on the inner surface of the sheath.

11. The lighted surgical access system of claim 1 wherein a distal end of the POF tail has an angled end profile.

12. The lighted surgical access system of claim 1 further comprising an end cap connected to a distal end of the POF tail.

13. The lighted surgical access system of claim 12 further comprising a reflective material attached to the end cap.

14. The lighted surgical access system of claim 1 wherein the sleeve is sealed to the distal portion of the sheath and is impermeable.

* * * * *